(12) United States Patent
Mangion et al.

(10) Patent No.: US 9,725,464 B2
(45) Date of Patent: Aug. 8, 2017

(54) PROCESS FOR PREPARING TETRACYCLIC HETEROCYCLE COMPOUNDS

(71) Applicant: MERCK SHARP & DOHME CORP., Rahway, NJ (US)

(72) Inventors: Ian Mangion, Cranford, NJ (US); Cheng-yi Chen, Princeton, NJ (US); Ingyu Jeon, Fanwood, NJ (US); Yonggang Chen, Westfield, NJ (US); Hongmei Li, Potomac, MD (US); Hoa N. Nguyen, Corona, CA (US); Peter E. Maligres, Fanwood, NJ (US); Artis Klapars, Edison, NJ (US); Ilia Zavialov, Furlong, PA (US); Nobuyoshi Yasuda, Mountainside, NJ (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 0 days.

(21) Appl. No.: 15/032,552

(22) PCT Filed: Oct. 24, 2014

(86) PCT No.: PCT/US2014/062091
§ 371 (c)(1),
(2) Date: Apr. 27, 2016

(87) PCT Pub. No.: WO2015/065821
PCT Pub. Date: May 7, 2015

(65) Prior Publication Data
US 2016/0257698 A1    Sep. 8, 2016

Related U.S. Application Data

(60) Provisional application No. 61/897,611, filed on Oct. 30, 2013, provisional application No. 61/973,648, filed on Apr. 1, 2014.

(51) Int. Cl.
| | |
|---|---|
| *C07D 498/04* | (2006.01) |
| *C07D 403/04* | (2006.01) |
| *C07C 215/50* | (2006.01) |
| *C07F 5/02* | (2006.01) |
| *C07C 213/02* | (2006.01) |

(52) U.S. Cl.
CPC .......... *C07D 498/04* (2013.01); *C07C 213/02* (2013.01); *C07C 215/50* (2013.01); *C07D 403/04* (2013.01); *C07F 5/025* (2013.01)

(58) Field of Classification Search
CPC .................................................... C07D 498/04
USPC .......................................................... 544/89
See application file for complete search history.

(56) References Cited

U.S. PATENT DOCUMENTS

| | | | |
|---|---|---|---|
| 2012/0083483 A1 | 4/2012 | Coburn et al. | |
| 2012/0252721 A1 | 10/2012 | Dousson et al. | |
| 2013/0280214 A1 | 10/2013 | Vacca et al. | |

FOREIGN PATENT DOCUMENTS

| | | | | |
|---|---|---|---|---|
| WO | 2012041014 A1 | 4/2012 | | |
| WO | WO 2012041014 A1 * | 4/2012 | ........... | C07D 471/04 |

* cited by examiner

*Primary Examiner* — Kahsay Habte
(74) *Attorney, Agent, or Firm* — Jeffrey P. Bergman; Catherine D. Fitch

(57) ABSTRACT

The present invention is directed to a process for preparing Tetracyclic Heterocycle Compounds of formula (I): which are useful as HCV NS5A inhibitors. The present invention is also directed to compounds that are useful as synthetic intermediates for making the compounds of formula (I).

(I)

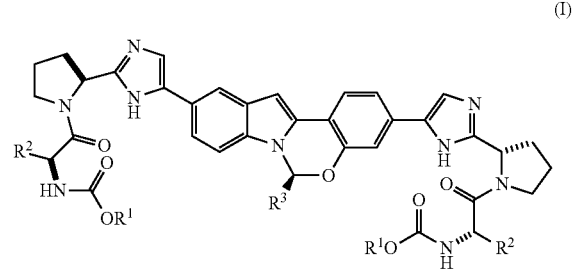

10 Claims, No Drawings

PROCESS FOR PREPARING TETRACYCLIC HETEROCYCLE COMPOUNDS

CROSS-REFERENCE TO RELATED APPLICATIONS

This application is the national stage application under 35 U.S.C. 371 of International Patent Application No. PCT/US2014/062091, filed Oct. 24, 2014, which claims priority to U.S. Provisional Patent Application No. 61/973,648, filed Apr. 1, 2014 and U.S. Provisional Patent Application No. 61/897,611, filed Oct. 30, 2013. Each of the aforementioned PCT and provisional applications is incorporated by reference in its entirety.

FIELD OF THE INVENTION

The present invention is directed to a process for preparing Tetracyclic Heterocycle Compounds which are useful as HCV NS5A inhibitors. The present invention is also directed to compounds that are useful as synthetic intermediates in the process of the invention.

BACKGROUND OF THE INVENTION

Various substituted tetracyclic heterocyclic compounds are inhibitors of the HCV NS5A enzyme. Included in these heterocycles are those related to Compound A, as defined and described below. These compounds and pharmaceutically acceptable salts thereof are useful in the treatment or prophylaxis of infection by HCV and in the treatment, prophylaxis, or delay in the onset or progression of HCV infection. Representative tetracyclic heterocyclic compounds that are useful for treating HCV infection are described, for example, in US Patent Publication No. US20120083483. Among the compounds disclosed in US20120083483 is dimethyl ((2S,2'S)-((2S,2'S)-2,2'-(5,5'-((S)-6-phenyl-6H-benzo [5,6][1,3]oxazino[3,4-a]indole-3,10-diyl)bis(1H-imidazole-5,2-diyl))bis(pyrrolidine-2,1-diyl))bis(3-methyl-1-oxobutane-2,1-diyl))dicarbamate, hereinafter referred to as Compound A. Compound A is a known inhibitor of HCV NS5A. The structure of Compound A is as follows:

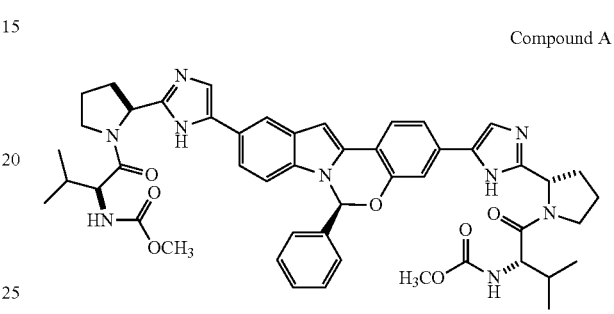

Compound A

US Patent Publication No. US20120083483 discloses methodology that can be employed to prepare Compound A and related tetracyclic HCV NS5A inhibitors. This general methodology is illustrated immediately below:

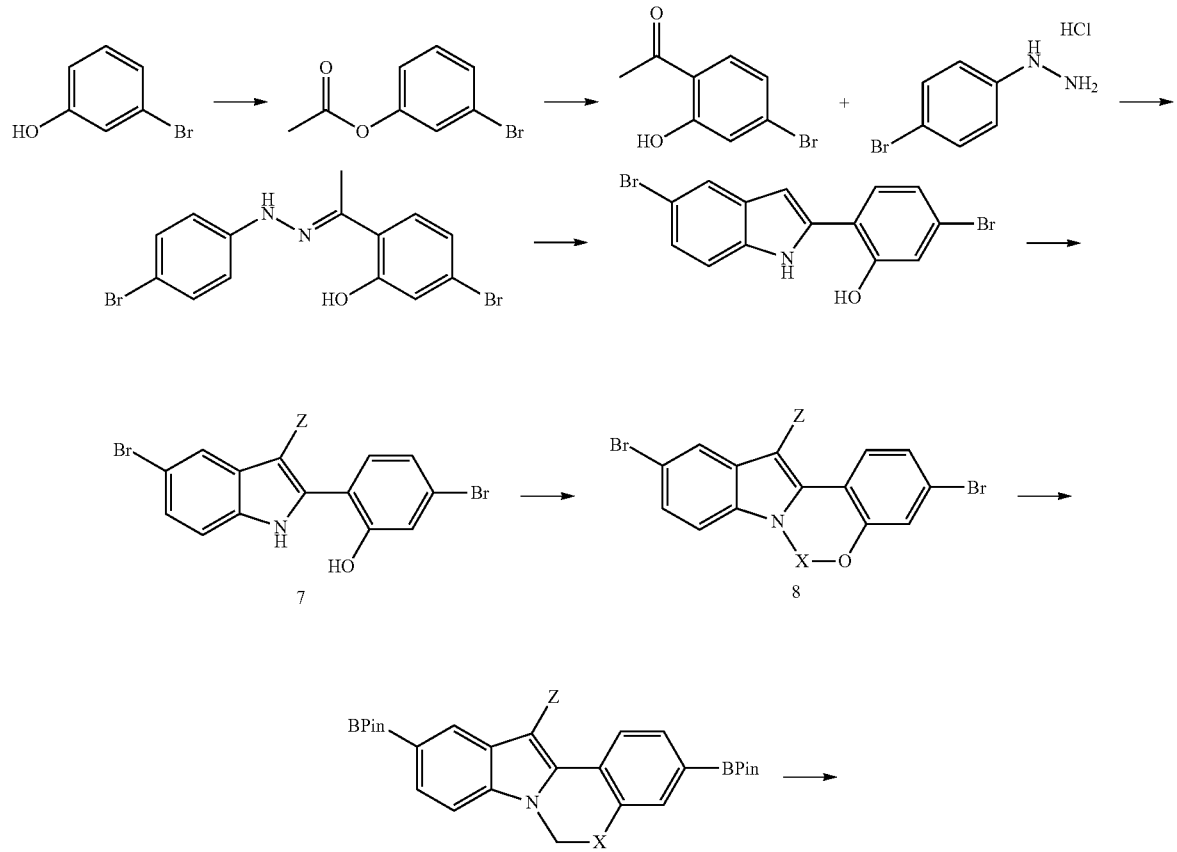

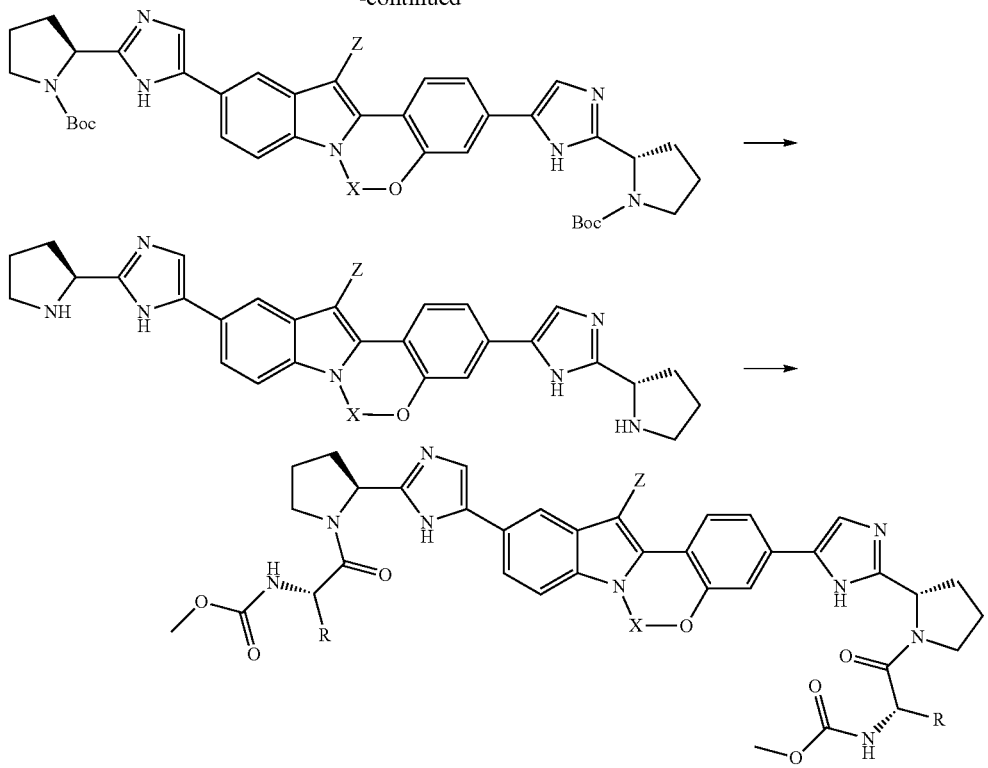

The methods described US Patent Publication No. US20120083483 are practical routes for the preparation of Compound A and related tetracyclic heterocyclic compounds. Nonetheless, there is always a need for alternative preparative routes which, for example, use reagents that are less expensive and/or easier to handle, consume smaller amounts of reagents, provide a higher yield of product, involve fewer steps, have smaller and/or more eco-friendly waste products, and/or provide a product of higher purity.

Unlike the disclosed methods for making tetracyclic HCV NS5A inhibitors described in US Patent Publication No. US20120083483, the process of the present invention employs fewer steps and provides an improved yield of Compound A with a high degree of stereoselectivity.

SUMMARY OF THE INVENTION

The present invention is directed to a process for preparing Tetracyclic Heterocycle Compounds of Formula (I) which are useful as HCV NS5A inhibitors. More particularly, the present invention includes a process (alternatively referred to herein as Process P) for preparing a compound of Formula I:

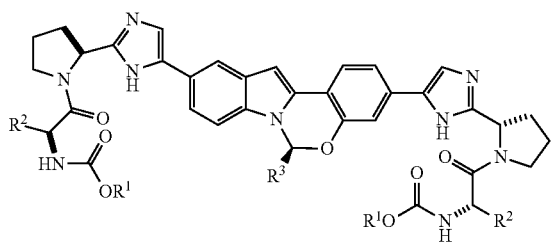

and pharmaceutically acceptable salts thereof, wherein:

each occurrence of $R^1$ is independently $C_1$-$C_6$ alkyl, $C_3$-$C_7$ cycloalkyl or $C_6$-$C_{10}$ aryl;

each occurrence of $R^2$ is independently $C_1$-$C_6$ alkyl, $C_3$-$C_7$ cycloalkyl, 3 to 7-membered monocyclic heterocycloalkyl or $C_6$-$C_{10}$ aryl; and $R^3$ is $C_1$-$C_6$ alkyl, $C_3$-$C_7$ cycloalkyl, $C_6$-$C_{10}$ aryl, 5 or 6-membered monocyclic heteroaryl or 9 or 10-membered bicyclic heteroaryl, wherein said $C_3$-$C_7$ cycloalkyl group, said $C_6$-$C_{10}$ aryl group, said 5 or 6-membered monocyclic heteroaryl group or said 9 or 10-membered bicyclic heteroaryl group can be optionally substituted with up to three groups, each independently selected from $C_1$-$C_6$ alkyl and $C_3$-$C_7$ cycloalkyl, and wherein said process comprises:

(A) contacting a compound of Formula II:

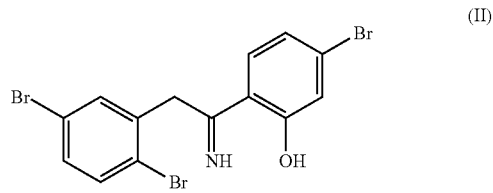 [SMILES: N=C(Cc1cc(Br)ccc1Br)c1ccc(Br)cc1O]

with a ruthenium-based catalyst in the presence of one of the following compounds: ammonium formate, ammonium acetate, ammonium benzoate, ammonium salicylate, $H(CH_3)_2SiOSi(CH_3)_2H$ or polymethylhydrosiloxane, in an organic solvent A to provide an amine compound of Formula III:

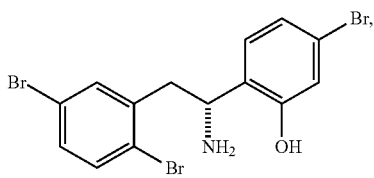

(III)

wherein organic solvent A is selected from acetonitrile, methanol, ethanol, isopropanol, tetrahydrofuran, 2-methyl tetrahydrofuran, toluene, chlorobenzene, dichloromethane and dichloroethane; and (B) contacting the compound of Formula III with a carbonate or phosphonate base; in the presence of a copper (I) salt in an organic solvent B to provide an indoline compound of Formula IV:

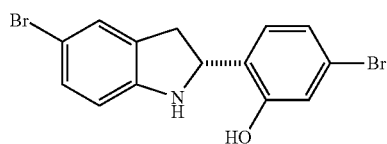

(IV)

wherein organic solvent B is selected from N,N-dimethylformamide, acetonitrile, dimethylacetamide, N-methyl pyrrolidinone and dimethylsulfoxide; and (C) contacting the compound of Formula IV with a compound of formula IVa:

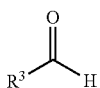

(IVa)

in the presence of an acid, in an organic solvent C to provide an tetracyclic compound of Formula V:

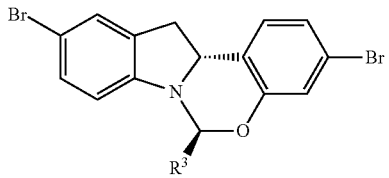

(V)

wherein organic solvent C is selected from acetonitrile, toluene, dichloromethane, tetrahydrofuran, 2-methyl tetrahydrofuran, ethyl acetate and isopropyl acetate; and (D) contacting the compound of Formula V with an oxidizing agent in the presence of an acid, in a mixture of water and organic solvent D to provide an indole compound of Formula VI:

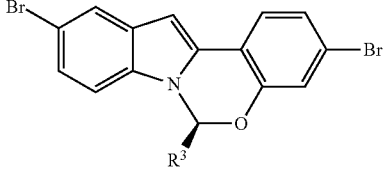

(VI)

wherein organic solvent D is selected from tetrahydrofuran, acetone, DMA, dichloromethane and toluene; and (E) (i) contacting the compound of Formula VI with bis(pinacoloato)diboron in the presence of an acetate or pivalate base, a transition metal catalyst, and optionally in the presence of a phosphorus ligand source, in an organic solvent E to provide an intermediate compound of Formula VII:

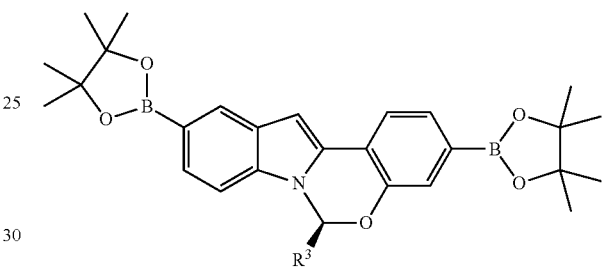

(VII)

and (ii) contacting the intermediate compound of formula VII with a compound of formula VIIb

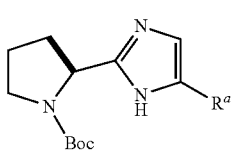

(VIIb)

in the presence of a carbonate, acetate or pivalate base and a transition metal catalyst, and optionally in the presence of a phosphorus ligand source, in mixture of water and organic solvent E' to provide a compound of formula VIII:

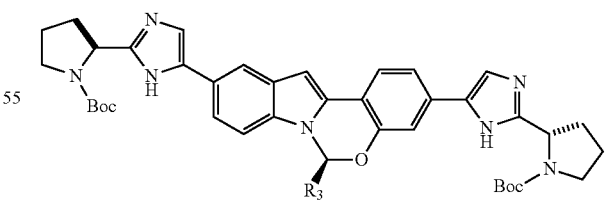

(VIII)

wherein organic solvents E and E' are selected from dimethylacetamide, toluene, acetonitrile, N,N-dimethylformamide, tetrahydrofuran, 2-methyl tetrahydrofuran, CPME, isopropanol, ethanol, ethyl acetate, isopropyl acetate and dimethoxyethane, and (F) contacting the di-p-nitrobenzoate salt of the compound of Formula VIII with an inorganic base, in an organic solvent F, for a time sufficient to remove the Boc protecting groups from the compound of Formula VIII, then the deprotected compound was contacted with HCl in said organic solvent F to provide a compound of Formula IX:

(IX)

wherein organic solvent F is selected from methanol, acetonitrile, tetrahydrofuran, 2-methyl tetrahydrofuran, ethanol, isopropanol and toluene; and (G) contacting the compound of Formula IX with an additive selected from 2-hydroxypyridine-N-oxide, N-hydroxysuccinimide, HOBt and pyridine, and a non-nucleophilic base) in the presence of a compound of formula Xa:

(Xa)

and an amide coupling reagent, in an organic solvent G to provide a compound of Formula I:

(I)

wherein organic solvent G is selected from tetrahydrofuran, N,N-dimethylformamide, dimethylacetamide, N-methylpyrrolidinone and dimethylsulfoxide;
and wherein
  each occurrence of $R^1$ is independently $C_1$-$C_6$ alkyl, $C_3$-$C_7$ cycloalkyl or $C_6$-$C_{10}$ aryl;
  each occurrence of $R^2$ is independently $C_1$-$C_6$ alkyl, $C_3$-$C_7$ cycloalkyl, 3 to 7-membered monocyclic heterocycloalkyl or $C_6$-$C_{10}$ aryl;
  $R^3$ is $C_1$-$C_6$ alkyl, $C_3$-$C_7$ cycloalkyl, $C_6$-$C_{10}$ aryl, 5 or 6-membered monocyclic heteroaryl or 9 or 10-membered bicyclic heteroaryl; and
  $R^a$ is Br, Cl or I.

Other embodiments, aspects and features of the present invention are either further described in or will be apparent from the ensuing description, examples, and appended claims.

DETAILED DESCRIPTION OF THE INVENTION

The present invention is directed to a process for preparing Tetracyclic Heterocycle Compounds of Formula (I) which are useful as HCV NS5A inhibitors. One aspect of the present invention is the process comprising Steps A through G as set forth above in the Summary of the Invention (i.e., Process P).

DEFINITIONS AND ABBREVIATIONS

The term "$C_1$-$C_6$ alkyl" as used herein, refers to an aliphatic hydrocarbon group, having from 1 to 6 carbon atoms wherein one of its hydrogen atoms is replaced with a bond. A $C_1$-$C_6$ alkyl group may be straight or branched and contain. Non-limiting examples of $C_1$-$C_6$ alkyl groups include methyl, ethyl, n-propyl, isopropyl, n-butyl, sec-butyl, isobutyl, tert-butyl, n-pentyl, neopentyl, isopentyl, n-hexyl, isohexyl and neohexyl. A $C_1$-$C_6$ alkyl group may be unsubstituted or substituted by one or more substituents which may be the same or different, each substituent being independently selected from the group consisting of halo, alkenyl, alkynyl, aryl, cycloalkyl, cyano, hydroxy, —O-alkyl, —O-aryl, -alkylene-O-alkyl, alkylthio, —NH₂, —NH(alkyl), —N(alkyl)₂, —NH(cycloalkyl), —O—C(O)-alkyl, —O—C(O)-aryl, —O—C(O)-cycloalkyl, —C(O)OH and —C(O)O-alkyl. In one embodiment, a $C_1$-$C_6$ alkyl group is linear. In another embodiment, a $C_1$-$C_6$ alkyl group is branched. Unless otherwise indicated, a $C_1$-$C_6$ alkyl group is unsubstituted.

The term "$C_6$-$C_{10}$ aryl" refers to phenyl and naphthyl. In one embodiment, an aryl group is phenyl.

The term "3 to 7-membered cycloalkyl" refers to a refers to a non-aromatic mono- or ring system comprising from about 3 to about 7 ring carbon atoms. Examples of "3 to 7-membered cycloalkyls include cyclopropyl, cyclobutyl, cyclopentyl, cyclohexyl and cycloheptyl. A 3 to 7-membered cycloalkyl group can be optionally substituted with one or more "ring system substituents" which may be the same or different, and are as defined herein below. In one embodiment, a 3 to 7-membered cycloalkyl group is unsubstituted. A ring carbon atom of a 3 to 7-membered cycloalkyl may be functionalized as a carbonyl group. An illustrative example of such a 3 to 7-membered cycloalkyl (also referred to herein as a "cycloalkanoyl" group) includes, but is not limited to, cyclobutanoyl:

The term "halo" as used herein, refers to fluorine, chlorine, bromine and iodine (alternatively referred to as fluoro, chloro, bromo, and iodo).

The term "5 or 6-membered monocyclic heteroaryl," as used herein, refers to an aromatic monocyclic ring system comprising about 5 to about 6 ring atoms, wherein from 1 to 4 of the ring atoms is independently O, N or S and the remaining ring atoms are carbon atoms. A 5 or 6-membered monocyclic heteroaryl group can be optionally substituted by one or more "ring system substituents" which may be the same or different, and are as defined herein below. A 5 or 6-membered monocyclic heteroaryl group is joined via a ring carbon atom, and any nitrogen atom of a heteroaryl can be optionally oxidized to the corresponding N-oxide. The term "5 or 6-membered monocyclic heteroaryl" also encompasses a 5 or 6-membered monocyclic heteroaryl group, as defined above, which is fused to a benzene ring. Non-limiting examples of 5 or 6-membered monocyclic heteroaryls include pyridyl, pyrazinyl, furanyl, thienyl, pyrimidinyl, pyridone (including N-substituted pyridones), isoxazolyl, isothiazolyl, oxazolyl, oxadiazolyl, thiazolyl, pyrazolyl, furazanyl, pyrrolyl, triazolyl, 1,2,4-thiadiazolyl, pyrazinyl, pyridazinyl, benzofurazanyl, indolyl, azaindolyl, benzimidazolyl, benzothienyl, imidazolyl, benzimidazolyl, thienopyridyl, thienopyrimidyl, pyrrolopyridyl, imidazopyridyl, isoquinolinyl, 1,2,4-triazinyl, benzothiazolyl and the like, and all isomeric forms thereof. Unless otherwise indicated, a 5 or 6-membered monocyclic heteroaryl group is unsubstituted.

The term "9 or 10-membered bicyclic heteroaryl," as used herein, refers to an aromatic bicyclic ring system comprising about 9 to about 10 ring atoms, wherein from 1 to 4 of the ring atoms is independently O, N or S and the remaining ring atoms are carbon atoms. A 9 or 10-membered bicyclic heteroaryl group can be optionally substituted by one or more "ring system substituents" which may be the same or different, and are as defined herein below. A 9 or 10-membered bicyclic heteroaryl group is joined via a ring carbon atom, and any nitrogen atom of a heteroaryl can be optionally oxidized to the corresponding N-oxide. Non-limiting examples of 9 or 10-membered bicyclic heteroaryls include and the like, and all isomeric forms thereof. Unless otherwise indicated, a 9 or 10-membered bicyclic heteroaryl group is unsubstituted.

Unless expressly stated to the contrary in a particular context, any of the various cyclic rings and ring systems described herein may be attached to the rest of the compound of which they are a part at any ring atom (i.e., any carbon atom or any heteroatom) provided that a stable compound results.

Unless expressly stated to the contrary, all ranges cited above are inclusive; i.e., the range includes the values for the upper and lower limits of the range as well as all values in between.

When any variable occurs more than one time in a compound involved in the process of the invention (e.g., $R^1$ or $R^2$), its definition on each occurrence is independent of its definition at every other occurrence. Also, combinations of substituents and/or variables are permissible only if such combinations result in a stable compound.

Unless expressly stated to the contrary, substitution by a named substituent is permitted on any atom in a ring (e.g., cycloalkyl, aryl, or heteroaryl) provided such ring substitution is chemically allowed and results in a stable compound.

In reference to the compounds employed as reactants or reagents in the process of the invention (e.g., Compounds II, III, and IV), a "stable" compound is one whose structure and properties remain or can be caused to remain essentially unchanged for a period of time sufficient to allow its use in the process of the invention so as to achieve the preparation of Compound of Formula (I). In reference to Compound of Formula (I), a "stable" compound is a compound which can be prepared in accordance with the process of the present invention and then isolated and whose structure and properties remain or can be caused to remain essentially unchanged for a period of time sufficient to allow use of the compound for its intended purpose; e.g., for the therapeutic administration to a subject who has HCV infection.

The following abbreviations are used below and have the following meanings: Ac is acetate, Am-phos is bis(di-tert-butyl(4-dimethylaminophenyl) phosphine), Boc or BOC is t-butoxy carbonyl, BrettPhos is 2-(dicyclohexylphosphino) 3,6-dimethoxy-2',4',6'-triisopropyl-1,1'-biphenyl, t-Bu is tertiary butyl, n-Bu is n-butyl, CataCXium A is di(1-adamantyl)-n-butylphosphine, Darco-KB is a brand of activated charcoal (Norit Americas, Inc.), DCC is dicyclohexylcarbodiimide, DCM is dichloromethane, DMA is N,N-dimethylacetamide, DME is dimethoxyethane, DTBPF is [1,1'-Bis(di-tert-butylphosphino)ferrocene]dichloropalladium(II), EDC is 1-ethyl-3-(3-dimethylaminopropyl)carbodiimide, EDTA is ethylenediaminetetraacetic acid, HATU is 1-[bis(dimethylamino)methylene]-1H-1,2,3-triazolo[4,5-b]pyridinium 3-oxid hexafluorophosphate, HOBt is hydroxybenzotriazole, HPLC is high performance liquid chromatography, N-Moc-valine is N-methoxycarbonyl-L-valine, MsOH is methanesulfonic acid, $PCy_3$ is tricyclohexylphosphine, $Pd_2dba_3$ is tris(dibenzylideneacetone)dipalladium(0), pin is pinacol, Piv is pivalate, (R,R)-teth-Ts-DPEN-RuCl is [N-[(1R,2R)-2-(amino-κN)-1,2-diphenylethyl]-4-methylbenzenesulfonamidato-κN]chloro [(1,2,3,4,5,6-η)-1,3,5-trimethylbenzene]-ruthenium, Sphos is 2-dicyclohexylphosphino-2',6'-dimethoxybiphenyl, T3P is propylphosphonic anhydride, TEMPO is (2,2,6,6-tetramethylpiperidin-1-yl)oxy, TFA is trifluoroacetic acid, TLC is thin-layer chromatography, TsOH is p-toluenesulfonic acid, and XPhos is 2-dicyclohexylphosphino-2',4',6'-triisopropylbiphenyl.

The Processes of the Present Invention

The present invention is directed to a process for preparing Tetracyclic Heterocycle Compounds of Formula (I) which are useful as HCV NS5A inhibitors. One aspect of the present invention is the process comprising Steps A through G as set forth above in the Summary of the Invention (i.e., Process P).

In another aspect, the present invention provides each individual step of Process P as a separate and individual embodiment (e.g. in one embodiment the present invention provides the process illustrated in Step A of Process P; in another embodiment the present invention provides the process illustrated in Step B of Process P, in still another embodiment the present invention provides the process illustrated in Step C of Process P, etc. . . . )

In still another aspect, the present invention provides a method ("Process A") for making Compounds of Formula (I):

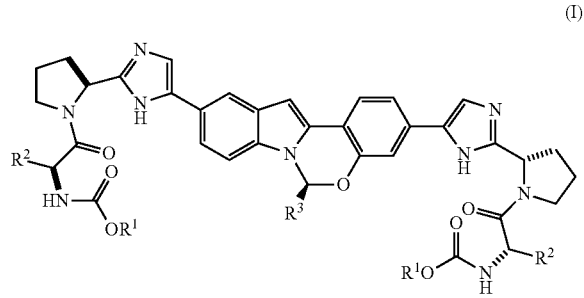

and pharmaceutically acceptable salts thereof, wherein said process comprises:

(A) contacting a compound of Formula IV:

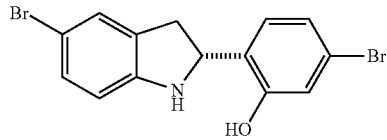

with a compound of formula IVa:

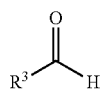

in the presence of an acid, in an organic solvent C, to provide a tetracyclic compound of Formula V:

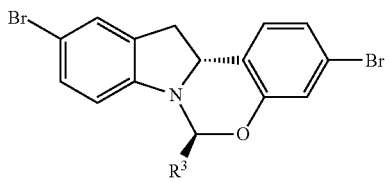

wherein organic solvent C is selected from acetonitrile, toluene, dichloromethane, tetrahydrofuran, 2-methyl tetrahydrofuran, ethyl acetate and isopropyl acetate; and (B) contacting the compound of Formula V with an oxidizing agent in the presence of a carbonate or phosphonate base, in a mixture of water and organic solvent D, to provide an indole compound of Formula VI:

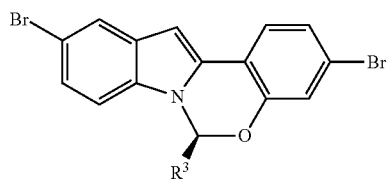

wherein organic solvent D is selected from tetrahydrofuran, acetone, DMA, dichloromethane and toluene; and (C) (i) contacting the compound of Formula VI with bis(pinacoloato)diboron in the presence of an acetate or pivalate base, a transition metal catalyst, and optionally in the presence of a phosphorus ligand source, in a mixture of water and an organic solvent E, to provide an intermediate compound of Formula VII:

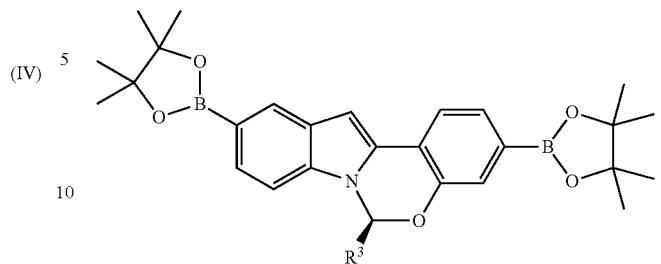

then (ii) contacting the intermediate compound of formula VII with a compound of formula VIIb

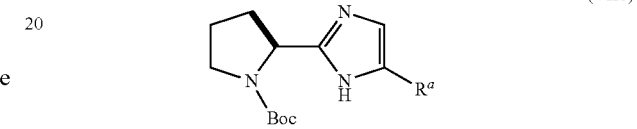

in the presence of a carbonate, acetate or pivalate base and a transition metal catalyst, and optionally in the presence of a phosphorus ligand source, in said mixture of water and organic solvent E, to provide a compound of formula VIII:

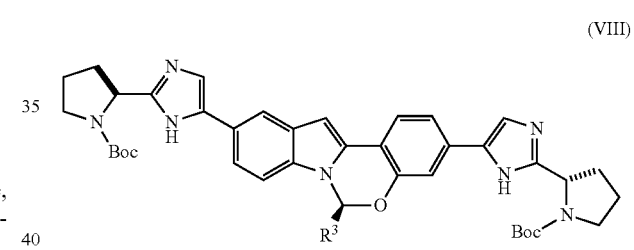

wherein organic solvent E is selected from dimethylacetamide, toluene, acetonitrile, N,N-dimethylformamide, tetrahydrofuran, 2-methyl tetrahydrofuran, cyclopentyl methyl ether, isopropanol, ethanol, ethyl acetate, isopropyl acetate and dimethoxyethane; and (D) (i) contacting the di-p-nitrobenzoate salt of the compound of Formula VIII with an inorganic base, in an organic solvent F, for a time sufficient to remove the Boc protecting groups from the compound of Formula VIII, then (ii) contacting the deprotected compound in situ with HCl to provide a compound of Formula IX:

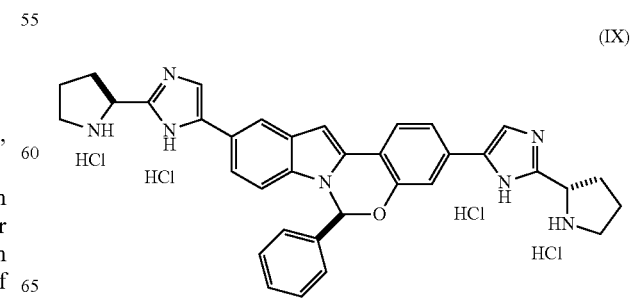

wherein organic solvent F is selected from methanol, acetonitrile, tetrahydrofuran, 2-methyl tetrahydrofuran, ethanol, isopropanol and toluene; and (E) contacting the compound of Formula IX with: (i) an additive selected from 2-hydroxypyridine-N-oxide, N-hydroxysuccinimide, HOBt and pyridine, and (ii) a non-nucleophilic base) in the presence of (i) a compound of formula Xa:

(Xa)

and (ii) an amide coupling reagent in an organic solvent G to provide a compound of Formula I:

(I)

wherein organic solvent G is selected from tetrahydrofuran, N,N-dimethylformamide, dimethylacetamide, N-methylpyrrolidinone and dimethylsulfoxide; and
wherein
each occurrence of $R^1$ is independently $C_1$-$C_6$ alkyl, $C_3$-$C_7$ cycloalkyl or $C_6$-$C_{10}$ aryl;
each occurrence of $R^2$ is independently $C_1$-$C_6$ alkyl, $C_3$-$C_7$ cycloalkyl, 3 to 7-membered monocyclic heterocycloalkyl or $C_6$-$C_{10}$ aryl;
$R^3$ is $C_1$-$C_6$ alkyl, $C_3$-$C_7$ cycloalkyl, $C_6$-$C_{10}$ aryl, 5 or 6-membered monocyclic heteroaryl or 9 or 10-membered bicyclic heteroaryl, wherein said $C_3$-$C_7$ cycloalkyl group, said $C_6$-$C_{10}$ aryl group, said 5 or 6-membered monocyclic heteroaryl group or said 9 or 10-membered bicyclic heteroaryl group can be optionally substituted with up to three groups, each independently selected from $C_1$-$C_6$ alkyl and $C_3$-$C_7$ cycloalkyl; and
$R^a$ is Br, Cl or I.

In one embodiment, for Process A, the acid employed in Step A is selected from TFA, MsOH, TsOH and HCl.

In another embodiment, for Process A, the acid employed in Step A is TFA.

In another embodiment, for Process A, Step A, is conducted at a temperature in a range of from about 20° C. to about 60° C.

In another embodiment, for Process A, Step A, the organic solvent C is acetonitrile.

In one embodiment, for Process A, Step B is conducted at a temperature in a range of from about −10° C. to about 70° C.

In another embodiment, for Process A, Step B, the organic solvent D is a mixture of water and DMA.

In one embodiment, for Process A, the oxidizing agent employed in Step B is selected from $KMnO_4$, ceric ammonium nitrate, $Mn(OAc)_2$/tBuOOH, $MnO_2$ and $Cu(OAc)_2$.

In another embodiment, for Process A, the oxidizing agent employed in Step B is $KMnO_4$.

In another embodiment, for Process A, the carbonate or phosponate base employed in Step B is selected from $KHCO_3$, $Na_2CO_3$, $K_2CO_3$, $Na_3HPO_4$, $K_3HPO_4$, $Na_2HPO_4$ and $K_2HPO_4$.

In another embodiment, for Process A, the carbonate or phosponate base employed in Step B is selected from $Na_2CO_3$ or $K_2CO_3$.

In one embodiment, for Process A, Step C, part (i) is conducted at a temperature in a range of from about 40° C. to about 110° C.;

In another embodiment, for Process A, the organic solvent employed in step C, part (i) is N,N-dimethylformamide;

In another embodiment, for Process A, the acetate or pivalate base employed in Step C, part (i) is selected from NaOAc, CsOAc, KOPiv, NaOPiv and potassium acetate.

In another embodiment, for Process A, the acetate or pivalate base employed in Step C, part (i) is potassium acetate.

In still another embodiment, for Process A, the transition metal catalyst employed in Step C, part (i) is selected from $Pd_2dba_3$, $Pd(OAc)_2$ and $PdCl_2$.

In another embodiment, for Process A, the transition metal catalyst employed in Step C, part (i) is $Pd_2dba_3$.

In another embodiment, for Process A, the optional phosphine ligand employed in Step C, part (i) is selected from $N-Bu(Ad)_2P$, Am-phos, $n-BuP(t-Bu)_2-HBF_4$, XPhos, SPhos, BrettPhos, DTBPF, $PCy_3$ and $P(t-Bu)_3$.

In yet another embodiment, for Process A, the optional phosphine ligand employed in Step C, part (i) is $N-Bu(Ad)_2P$.

In one embodiment, for Process A, Step C, part (ii) is conducted at a temperature in a range of from about 40° C. to about 110° C.

In another embodiment, for Process A, in step C, part (ii), for compound (VIIb), Ra is Cl.

In another embodiment, for Process A, in step C, part (ii), for compound (VIIb), Ra is I.

In another embodiment, for Process A, in step C, part (ii), for compound (VIIb), Ra is Br.

In another embodiment, for Process A, the organic solvent employed in step C, part (ii) is N,N-dimethylformamide.

In another embodiment, for Process A, the carbonate, acetate or pivalate base employed in Step C, part (ii) is selected from $K_2CO_3$, NaOAc, CsOAc, KOPiv, NaOPiv and potassium acetate.

In still another embodiment, for Process A, the carbonate, acetate or pivalate base employed in Step C, part (ii) is $K_2CO_3$.

In another embodiment, for Process A, the transition metal catalyst employed in Step C, part (ii) is selected from $Pd_2dba_3$, $Pd(OAc)_2$ and $PdCl_2$.

In yet another embodiment, for Process A, the transition metal catalyst employed in Step C, part (ii) is $Pd_2dba_3$.

In another embodiment, for Process A, the optional phosphine ligand employed in Step C, part (ii) is selected from $N-Bu(Ad)_2P$, Am-phos, $n-BuP(t-Bu)_2-HBF_4$, XPhos, SPhos, BrettPhos, DTBPF, $PCy_3$ and $P(t-Bu)_3$.

In another embodiment, for Process A, the optional phosphine ligand employed in Step C, part (ii) is Am-phos.

In one embodiment, for Process A, Step D, part (i) is conducted at a temperature in a range of from about 0° C. to about 60° C.

In another embodiment, for Process A, the organic solvent employed in step D is N,N-dimethylformamide.

In another embodiment, for Process A, the inorganic base employed in step D is selected from a carbonate base, a phosponate base or an alkali metal hydroxide base.

In still another embodiment, for Process A, the inorganic base employed in step D is selected $K_2CO_3$, $Na_2CO_3$, NaOH, KOH, $Na_3PO_4$ and $K_3PO_4$.

In another embodiment, for Process A, Step D, part (ii) is conducted at a temperature in a range of from about 20° C. to about 60° C.;

In one embodiment, for Process A, Step E is conducted at a temperature in a range of from about −10° C. to about 60° C.

In another embodiment, for Process A, the organic solvent employed in step E is N,N-dimethylformamide.

In another embodiment, for Process A, the non-nucleophilic base employed in step E is selected from N-methylmorpholine, triethylamine, diisopropylethylamine and pyridine.

In still another embodiment, for Process A, the non-nucleophilic base employed in step E is N-methylmorpholine.

In another embodiment, for Process A, the amide coupling reagent employed in step E is selected from DCC, HATU, T3P and N-(3-dimethylaminopropyl)-N'-ethylcarbodiimide hydrochloride.

In yet another embodiment, for Process A, the amide coupling reagent employed in step E is N-(3-dimethylaminopropyl)-N'-ethylcarbodiimide hydrochloride.

In another embodiment, for Process A, the organic solvent employed in step E is acetonitrile.

In another embodiment, for Process A, the additive employed in step E is HOBt.

In another embodiment, for Process A, each occurrence of $R^1$ and $R^2$ is independently $C_1$-$C_6$ alkyl and $R^3$ is 5 or 6-membered heteroaryl or $C_6$-$C_{10}$ aryl, wherein $R^3$ can be optionally substituted with a group selected from $C_1$-$C_6$ alkyl and $C_3$-$C_7$ cycloalkyl.

In another embodiment, for Process A:

Step A is conducted at a temperature in a range of from about 25° C. to about 40° C.;
organic solvent C is acetonitrile;
the acid employed in Step A is TFA;
Step B is conducted at a temperature in a range of from about 0° C. to about 20° C.;
organic solvent D is a mixture of water and DMA;
the oxidizing agent employed in Step B is $KMnO_4$;
the carbonate or phosponate base employed in Step B is $Na_2CO_3$ or $K_2CO_3$;
Step C, part (i) is conducted at a temperature in a range of from about 70° C. to about 90° C.;
the organic solvent employed in step C, part (i) is a mixture of DME and water;
the acetate or pivalate base employed in Step C, part (i) is selected from NaOAc, CsOAc and potassium acetate;
the transition metal catalyst employed in Step C, part (i) is $Pd_2dba_3$;
the optional phosphine ligand employed in Step C, part (i) is $N$-$Bu(Ad)_2P$;
Step C, part (ii) is conducted at a temperature in a range of from about 70° C. to about 90° C.;
the organic solvent employed in step C, part (ii) is a mixture of DME and water;
the carbonate, acetate or pivalate base employed in Step C, part (ii) is $Na_2CO_3$ or $K_2CO_3$;
the transition metal catalyst employed in Step C, part (ii) is $Pd_2dba_3$;
the optional phosphine ligand employed in Step C, part (ii) is Am-phos;
Step D, part (i) is conducted at a temperature in a range of from about 15° C. to about 30° C.;
the organic solvent employed in step D is an organic alcohol;
the inorganic base employed in step D is an alkali metal carbonate base;
Step D, part (ii) is conducted at a temperature in a range of from about 35° C. to about 50° C.;
Step E is conducted at a temperature in a range of from about 15° C. to about 35° C.;
the organic solvent employed in step E is acetonitrile;
the additive employed in step E is HOBt;
the non-nucleophilic base employed in step E is N-methylmorpholine;
the amide coupling reagent employed in step E is N-(3-dimethylaminopropyl)-N'-ethylcarbodiimide hydrochloride.

In still another embodiment, for Process A,

Step A is conducted at a temperature in a range of from about 25° C. to about 40° C.;
organic solvent C is acetonitrile;
the acid employed in Step A is TFA;
Step B is conducted at a temperature in a range of from about 0° C. to about 20° C.;
organic solvent D is a mixture of water and DMA;
the oxidizing agent employed in Step B is $KMnO_4$;
the carbonate or phosponate base employed in Step B is $Na_2CO_3$ or $K_2CO_3$;
Step C, part (i) is conducted at a temperature in a range of from about 70° C. to about 90° C.;
the organic solvent employed in step C, part (i) is a mixture of DME and water;
the acetate or pivalate base employed in Step C, part (i) is selected from NaOAc, CsOAc and potassium acetate;
the transition metal catalyst employed in Step C, part (i) is $Pd_2dba_3$;
the optional phosphine ligand employed in Step c, part (i) is $N$-$Bu(Ad)_2P$;
Step C, part (ii) is conducted at a temperature in a range of from about 70° C. to about 90° C.;
the organic solvent employed in step C, part (ii) is a mixture of DME and water;
the carbonate, acetate or pivalate base employed in Step C, part (ii) is $Na_2CO_3$ or $K_2CO_3$;
the transition metal catalyst employed in Step C, part (ii) is $Pd_2dba_3$;
the optional phosphine ligand employed in Step C, part (ii) is Am-phos;
Step D, part (i) is conducted at a temperature in a range of from about 15° C. to about 30° C.;
the organic solvent employed in step D is an organic alcohol;
the inorganic base employed in step D is an alkali metal carbonate base;
Step D, part (ii) is conducted at a temperature in a range of from about 35° C. to about 50° C.;
Step E is conducted at a temperature in a range of from about 15° C. to about 35° C.;
the organic solvent employed in step E is acetonitrile;
the additive employed in step E is HOBt;
the non-nucleophilic base employed in step E is N-methylmorpholine;

the amide coupling reagent employed in step E is N-(3-dimethylaminopropyl)-N'-ethylcarbodiimide hydrochloride.

In another embodiment, the present invention provides a process ("Process B") for preparing a compound of Formula III:

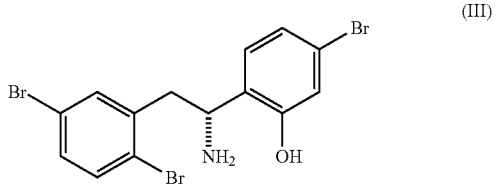 [SMILES: N[C@H](Cc1cc(Br)ccc1Br)c1ccc(Br)cc1O]

which comprises contacting a compound of Formula II:

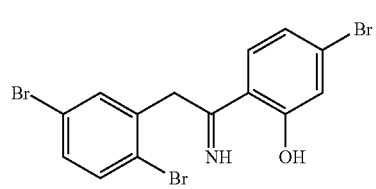

with a ruthenium-based catalyst in the presence of one of the following compounds: ammonium formate, ammonium acetate, ammonium benzoate, ammonium salicylate, $H(CH_3)_2SiOSi(CH_3)_2H$ or polymethylhydrosiloxane, in an organic solvent A to provide an amine compound of Formula III, wherein organic solvent A is selected from acetonitrile, methanol, ethanol, isopropanol, tetrahydrofuran, 2-methyl tetrahydrofuran, toluene, chlorobenzene, dichloromethane and dichloroethane.

In one embodiment, for Process B:
said process is conducted in the presence of ammonium formate at a temperature in a range of from about 40° C. to about 80° C.;
organic solvent A is dichloromethane; and
the ruthenium based catalyst is selected from Ts-DENEB-RuCl, benzenesulfonyl-DENEB-RuCl and

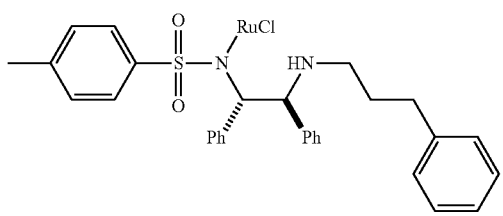

In another embodiment, the present invention provides a process ("Process C") for preparing a compound of Formula V:

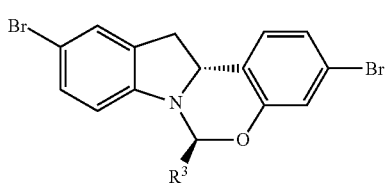

which comprises contacting a compound of Formula IV:

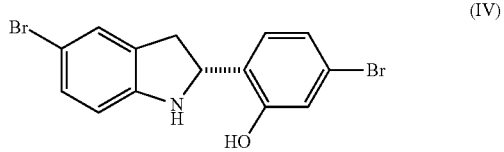 [SMILES: Oc1cc(Br)ccc1[C@H]1Cc2cc(Br)ccc2N1]

with a compound of formula IVa:

in the presence of an acid, in an organic solvent C to provide a compound of Formula V, wherein organic solvent C is selected from acetonitrile, toluene, dichloromethane, tetrahydrofuran, 2-methyl tetrahydrofuran, ethyl acetate and isopropyl acetate.

In one embodiment, for Process C:
said process is conducted at a temperature in a range of from about 20° C. to about 60° C.;
organic solvent C is acetonitrile;
the acid employed is selected from TFA, MsOH, TsOH and HCl.

In another embodiment, the present invention provides a process ("Process D") for preparing a compound of Formula VI:

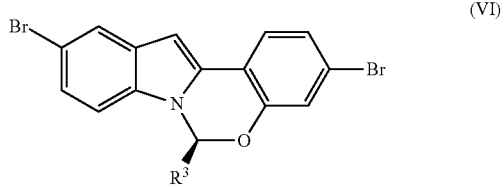

which comprises contacting a compound of Formula V:

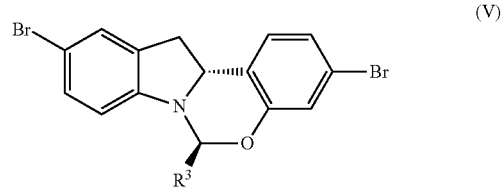

with an oxidizing agent, in the presence of a carbonate or phosphonate base, in a mixture of water and organic solvent D to provide the compound of Formula VI, wherein organic solvent D is selected from tetrahydrofuran, acetone, DMA, dichloromethane and toluene.

In one embodiment, for Process D:
said process is conducted at a temperature in a range of from about −10° C. to about 70° C.;
organic solvent D is a mixture of water and DMA;
the oxidizing agent employed is selected from $KMnO_4$, ceric ammonium nitrate, $Mn(OAc)_2$/tBuOOH, $MnO_2$ and $Cu(OAc)_2$;

the carbonate or phosponate base employed is selected from KHCO$_3$, Na$_2$CO$_3$, K$_2$CO$_3$, Na$_3$HPO$_4$, K$_3$HPO$_4$, Na$_2$HPO$_4$ and K$_2$HPO$_4$.

In one embodiment, for any of processes A, B, C or D, each occurrence of R$^1$ and R$^2$ is C$_1$-C$_6$ alkyl.

In another embodiment, for any of processes A, B, C or D, each occurrence of R$^1$ is methyl and each occurrence of R$^2$ is isopropyl.

In another embodiment, for any of processes A, B, C or D, each occurrence of R$^1$ is methyl, each occurrence of R$^2$ is isopropyl and R$^3$ is phenyl In one embodiment, for Process A, the compound of formula (I) being prepared is Compound A:

Compound A

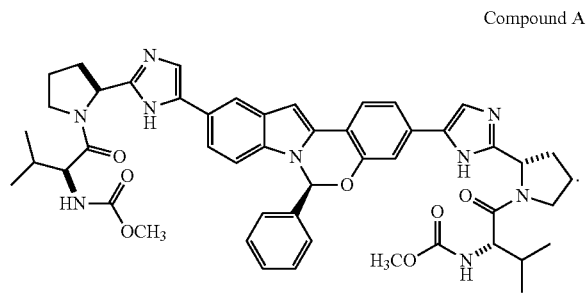

In one embodiment the invention provides a process for preparing Compound A:

Compound A

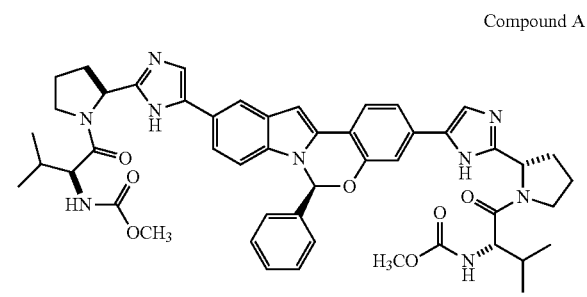

wherein said process comprises the steps:

(A) contacting an intermediate compound of formula VII:

(VII)

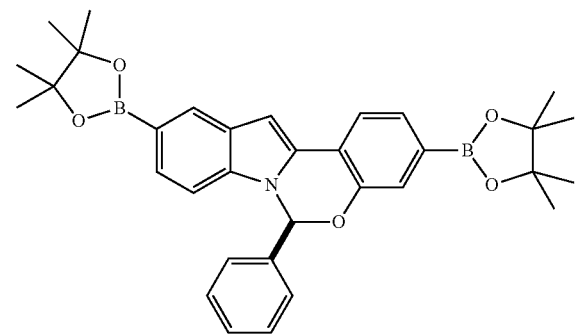

with a compound of formula VIIb (VIIb)

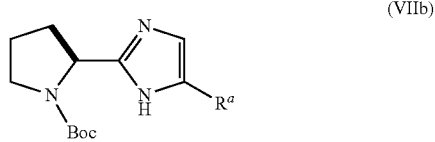

wherein Ra is Br, Cl or I, in the presence of a carbonate, acetate or pivalate base and a transition metal catalyst, and optionally in the presence of a phosphorus ligand source, in said mixture of water and organic solvent E, to provide a compound of formula VIII:

(VIII)

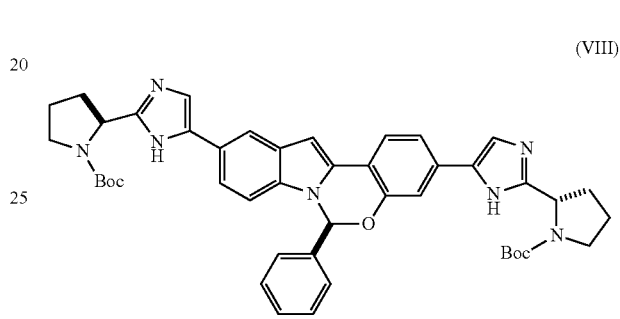

wherein organic solvent E is selected from dimethylacetamide, toluene, acetonitrile, N,N-dimethylformamide, tetrahydrofuran, 2-methyl tetrahydrofuran, cyclopentyl methyl ether, isopropanol, ethanol, ethyl acetate, isopropyl acetate and dimethoxyethane; and (D) (i) contacting the di-p-nitrobenzoate salt of the compound of Formula VIII with an inorganic base, in an organic solvent F, for a time sufficient to remove the Boc protecting groups from the compound of Formula VIII, then (ii) contacting the deprotected compound in situ with HCl to provide a compound of Formula IX:

(IX)

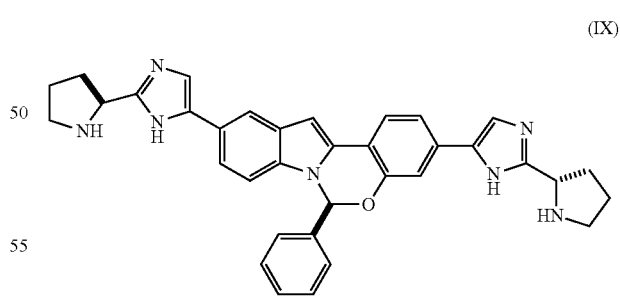

wherein organic solvent F is selected from methanol, acetonitrile, tetrahydrofuran, 2-methyl tetrahydrofuran, ethanol, isopropanol and toluene; and (E) contacting the compound of Formula IX with: (i) an additive selected from 2-hydroxypyridine-N-oxide, N-hydroxysuccinimide, HOBt and pyridine, and (ii) a non-nucleophilic base) in the presence of (i) a compound of formula Xa:

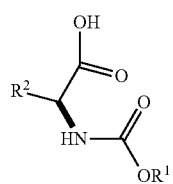

(Xa)

and (ii) an amide coupling reagent in an organic solvent G to provide Compound A, wherein organic solvent G is selected from tetrahydrofuran, N,N-dimethylformamide, dimethylacetamide, N-methylpyrrolidinone and dimethylsulfoxide.

In one embodiment, for the above process for making Compound A, group $R^a$ on compound (VIIb) is Cl.

In another embodiment, for the above process for making Compound A, group $R^a$ on compound (VIIb) is I.

In another embodiment, for the above process for making Compound A, group $R^a$ on compound (VIIb) is Br.

The present invention also provides synthetic intermediates useful for making the Compounds of Formula (I).

In one embodiment, the present invention provides a compound having the structure:

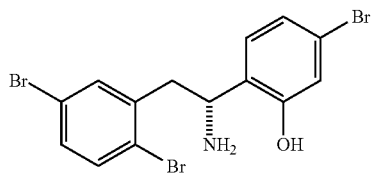

or a pharmaceutically acceptable salt thereof.

In another embodiment, the present invention provides a compound having the structure:

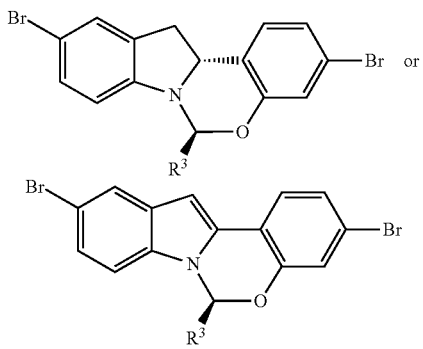

or a pharmaceutically acceptable salt thereof. This compound is useful as a synthetic intermediate for making Compounds of Formula (I).

In another embodiment, the present invention provides a compound having the structure:

or a pharmaceutically acceptable salt thereof, wherein $R^3$ is $C_1$-$C_6$ alkyl, $C_3$-$C_7$ cycloalkyl, $C_6$-$C_{10}$ aryl, 5 or 6-membered monocyclic heteroaryl or 9 or 10-membered bicyclic heteroaryl, wherein said $C_3$-$C_7$ cycloalkyl group, said $C_6$-$C_{10}$ aryl group, said 5 or 6-membered monocyclic heteroaryl group or said 9 or 10-membered bicyclic heteroaryl group can be optionally substituted with up to three groups, each independently selected from $C_1$-$C_6$ alkyl and $C_3$-$C_7$ cycloalkyl.

In another embodiment, the present invention provides a compound having the structure:

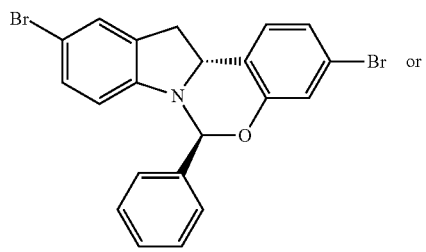

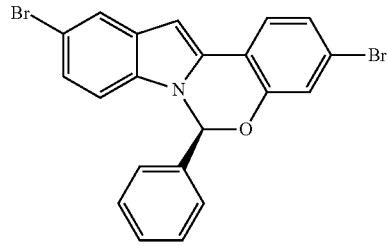

or a pharmaceutically acceptable salt thereof. Such compounds are useful as synthetic intermediates for making Compounds of Formula (I), wherein $R^3$ is phenyl.

In still another embodiment, the present invention provides a compound having the structure:

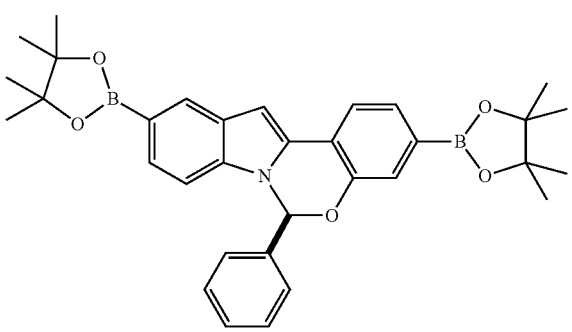

or a pharmaceutically acceptable salt thereof. This compound is useful as a synthetic intermediate for making Compounds of Formula (I), wherein $R^3$ is phenyl.

In another embodiment, the present invention provides a compound having the structure:

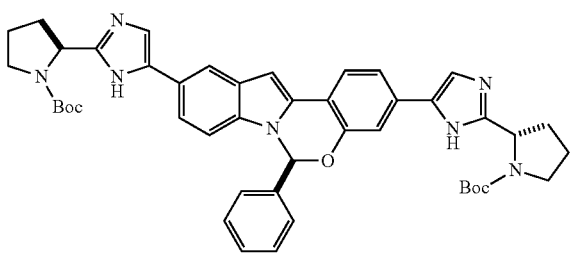

or a pharmaceutically acceptable salt thereof. This compound is useful as a synthetic intermediate for making Compounds of Formula (I), wherein $R^3$ is phenyl.

In yet another embodiment, the present invention provides a compound having the structure:

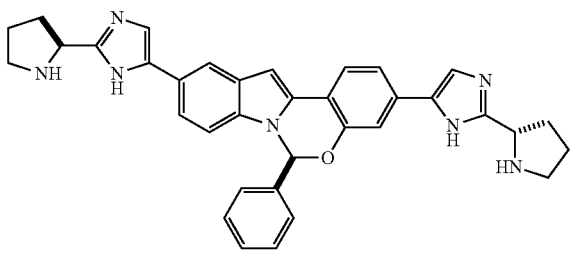

or a pharmaceutically acceptable salt thereof. This compound is useful as a synthetic intermediate for making Compounds of Formula (I), wherein $R^3$ is phenyl.

In one embodiment, any step of any of the processes described herein can be conducted in any organic solvent.

EXAMPLES

General Methods

Solvents, reagents, and intermediates that are commercially available were used as received. Reagents and intermediates that are not commercially available were prepared in the manner as described below. $^1$H NMR spectra were obtained on a Bruker Avance 500 (500 MHz) and are reported as ppm downfield from $Me_4Si$ with number of protons, multiplicities, and coupling constants in Hertz indicated parenthetically. Where LC/MS data are presented, analyses was performed using an Applied Biosystems API-100 mass spectrometer and Shimadzu SCL-10A LC column: Altech platinum C18, 3 micron, 33 mm×7 mm ID; gradient flow: 0 minutes—10% $CH_3CN$, 5 minutes—95% $CH_3CN$, 5-7 minutes—95% $CH_3CN$, 7 minutes—stop. The retention time and observed parent ion are given. Flash column chromatography was performed using pre-packed normal phase silica from Biotage, Inc. or bulk silica from Fisher Scientific. Unless otherwise indicated, column chromatography was performed using a gradient elution of hexanes/ethyl acetate, from 100% hexanes to 100% ethyl acetate.

Example 1

Preparation of Intermediate Compound 2

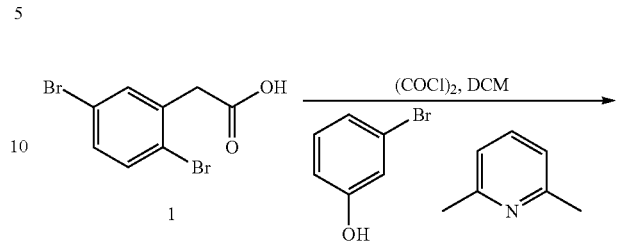

A 2 L 3-neck round-bottomed flask equipped with overhead stirring and a nitrogen inlet was charged with acid 1 (100 g, 339 mmol) and dichloromethane (1200 mL, 12 vol) at ambient temperature. After all solids were dissolved, N,N-dimethylformamide (1.24 g, 0.05 equiv) was added followed by slow addition of oxalyl chloride (48.3 g, 1.1 equiv) over 20 minutes at ambient temperature. The resulting mixture was stirred under nitrogen at ambient temperature for 1 hour and monitored by HPLC for complete conversion. After the reaction was complete, batch volume was concentrated to 500 mL.

A separate 2 L 3-neck round-bottomed flask equipped with overhead stirring and a nitrogen inlet was charged with acid 3-bromophenol (62.9 g, 356 mmol, 1.05 equiv) and dichloromethane (530 mL, 5 vol). 2,6-Lutidine (73.5 g, 2.0 equiv) was charged maintaining temperature below 25° C., and the resulting mixture was cooled to 0-5° C. The solution of acyl chloride in dichloromethane generated above was charged slowly while maintaining batch temperature at between 0 and 5° C. The resulting mixture was stirred for 1 hour and monitored by HPLC for complete conversion.

After the reaction was complete, the batch was quenched with 1N HCl solution (530 ml). The aqueous layer was cut, and the organics were washed with water (530 ml). The volume of organics was then reduced to 300 mL and dichloromethane was replaced with acetonitrile via continuous distillation. During the solvent swap, the solution of 2 becomes a slurry. At this time, water (318 ml) was charged slowly over 30 minutes, and the resulting slurry was stirred for 60 minutes. The slurry was then filtered and washed with 50% acetonitrile/water (318 ml). After drying under vacuum and nitrogen sweeping, 146.0 g (91% yield) of the title compound was obtained as a white crystalline solid. $^1$H NMR ($CDCl_3$, 400 MHz): δ=7.54 (d, J=3.0 Hz, 1H), 7.49 (d, J=10.6 Hz, 1H), 7.39 (dd, J=10.0, 2.4 Hz, 1H), 7.35-7.32 (m, 2H), 7.25 (d, J=10.1 Hz, 1H), 7.10 (dd, J=10.6, 1.6 Hz, 1H), 4.00 (s, 2H).

Example 2

Preparation of Intermediate Compound 3

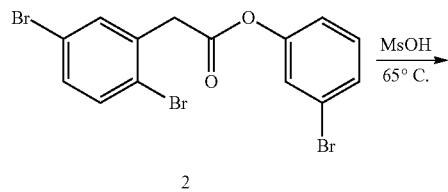

A 2 L 3-neck round-bottomed flask equipped with overhead stirring and a nitrogen inlet was charged with methanesulfonic anhydride (10.61 g, 59.1 mmol, 0.2 equiv) and methanesulfonic acid (384 mL, 20 equiv) at ambient temperature. The resulting mixture was stirred and heated to 90° C. After 1 hour holding at 90° C., the mixture was cooled to 65° C., and 2 (132.5 g, 295 mmol) was charged under nitrogen and the resulting mixture was stirred for 22 to 24 hours at 65° C. At this time TLC indicated completion, and the batch was cooled to room temperature followed by addition of isopropanol/water (3:1, 1115 ml, 8×vol) while maintaining batch temperature below 50° C. The slurry was then stirred for 20 minutes and filtered. The wet cake was washed with isopropanol/water (1:1, 418 ml). After drying under vacuum and nitrogen sweeping at 60 to 70° C. for at least 12 hours, 108.0 g (82% yield) of desired product 3 was obtained as a white crystalline solid. $^1$H NMR (500 MHz, DMSO-$d_6$): δ=11.60 (s, 1H), 7.87 (d, J=8.5 Hz, 1H), 7.67 (d, J=2.4 Hz, 1H), 7.59 (d, J=8.7 Hz, 1H), 7.45 (dd, J=8.7, 2.4 Hz, 1H), 7.26 (d, J=1.9 Hz, 1H), 7.20 (dd, J=8.4, 1.8 Hz, 1H), 4.59 (s, 2H).

Example 3

Preparation of Intermediate Compound 4

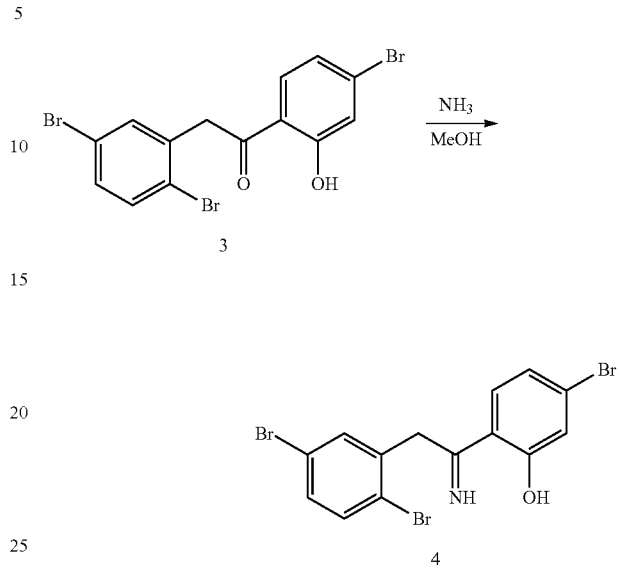

A 500 mL round-bottomed flask equipped with overhead stirring and a nitrogen inlet was charged with ketone 3 (37.1 g., 83 mmol) and 7N ammonia in methanol solution (201 mL, 1.405 mol, 17 equiv). On addition of the ammonia the white ketone is observed to turn yellow and the suspension remains yellow throughout the reaction. The mixture was stirred vigorously under nitrogen at room temperature for 20 hours and monitored by HPLC for complete conversion.

When conversion was complete, the suspension of imine 4 was filtered and the collected yellow crystalline solids rinsed with a minimal amount of methanol (mother liquor loss=1.92 g. or 5.2%). The solids were dried with a nitrogen sweep to <1 wt % methanol and weighed (33.6 g., 91% yield) and taken on to the next step. $^1$H NMR (CDCl$_3$, 400 MHz): δ=9.97, (s, 1H), 7.56 (d, J=9.1 Hz, 1H), 7.48 (d, J=8.6 Hz, 1H), 7.42 (d, J=2.4 Hz, 1H), 7.40 (d, J=2.4 Hz, 1H), 7.22 (d, J=2.0 Hz, 1H), 7.02 (dd, J=8.6, 2.0 Hz, 1H), 4.22 (s, 2H).

Example 4

Preparation of Intermediate Compound 5

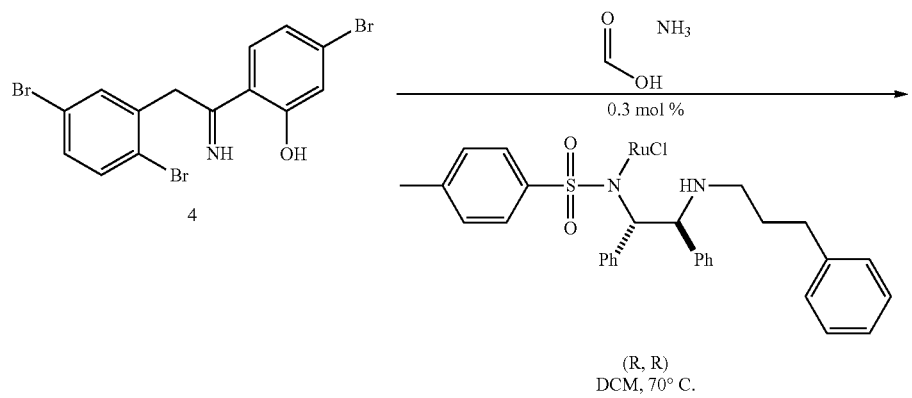

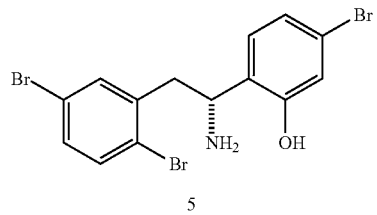

5

A 1 L Parr shaker was charged with imine 4 (38.8 g., 87 mmol), ammonium formate (10.92 g., 173 mol, 2.0 equiv), and (R,R)Teth-Ts-DPEN-RuCl (161 mg, 0.260 mmol, 0.3 mol %, 0.003 equiv), and the flask was purged with nitrogen for 10 minutes. Separately, dichloromethane (427 mL, 11 vol) was degassed with nitrogen then added under nitrogen to the vessel containing 4. When addition of solvent was complete, the mixture was heated to 70° C. and stirred under nitrogen for 24 hours, monitoring for conversion by HPLC.

Upon completion, the reaction was cooled to room temperature and neutralized to pH=7.5 with 10 wt % NaHCO₃ aqueous solution. The aqueous layer was cut, and the organics washed 2× with 3 volumes (30 mL) water. The organics were concentrated and the solvent switched to acetonitrile (194 mL, 5 vol) and seeded. After 1 hour of stirring the formation of a seed bed was verified, and then water (155 mL, 4 vol) was added slowly over 1 hour. The resulting crystals were collected by filtration and dried under a nitrogen sweep, providing 5 as a white solid (33.1 g., 73.6 mmol, 85% yield, 99% ee). ¹H NMR (CDCl₃, 400 MHz): δ=7.46 (d, J=8.4 Hz, 1H), 7.27 (m, 1H), 7.22 (d, J=2.4 Hz, 1H), 7.06 (d, J=1.9 Hz, 1H), 6.87 (dd, J=8.1, 2.0 Hz, 1H), 6.70 (d, J=8.1 Hz, 1H), 4.45 (dd, J=8.8, 5.7 Hz, 1H), 3.15 (m, 2H).

Example 5

Preparation of Intermediate Compound 6

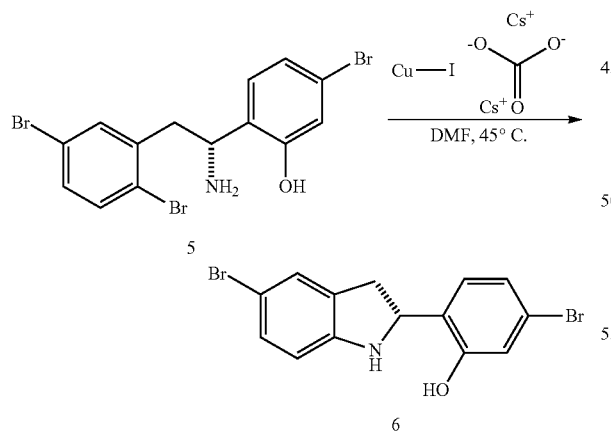

A 500 mL round-bottomed flask equipped with a magnetic stir bar, a thermocouple, and a nitrogen inlet was charged with amine 5 (33.0 g., 73.3 mmol), copper iodide (698 mg., 3.67 mmol, 0.05 equiv) and cesium carbonate (47.8 g., 147 mmol, 2.0 equiv), and the flask was purged with nitrogen for 10 minutes. In a separate flask, N,N-dimethylformamide (165 mL, 5.0 vol) was sparged with nitrogen for 30 minutes, then added via cannula under nitrogen to the flask containing 5. When addition of solvent was complete, the mixture was heated to 45° C. and stirred under nitrogen for 1 hour, monitoring for conversion by HPLC.

When conversion was complete (typically <60 minutes), the reaction was cooled to room temperature and diluted with 20 volumes ethyl acetate (100 mL) and immediately neutralized with 25 wt % aqueous ammonium chloride with vigorous stirring. The aqueous layer will turn blue as copper is solubilized. The pH is further adjusted to pH=7.5 with 1N HCl. The aqueous layer was cut, and back-extracted with 2 volumes EtOAC, and the combined organics washed successively with 4 volumes of 10 wt % sodium chloride and 4 volumes of water. The organics were then concentrated with a continuous solvent switch to acetonitrile (target final volume of 5 volumes acetonitrile, <5% residual ethyl acetate). Over this time, white crystals of 6 were observed to precipitate forming a seed bed. When the target volume was reached, 5 volumes of water was added slowly over 60 minutes with stirring. When the water addition was complete, the slurry was stirred for a further 1 hour, then the solids collected by filtration and washed with 1 volume of 1:1 acetonitrile:water, then dried via nitrogen sweep, providing 6 as a white crystalline solid (24.6 g., 66.7 mmol, 91% yield, 99% ee). ¹H NMR (CDCl₃, 400 MHz): δ=9.58 (s, 1H), 7.31 (s, 1H), 7.25 (d, J=8.3 Hz, 1H), 7.10 (d, J=2.0 Hz, 1H), 6.98 (dd, J=8.0, 2.0 Hz, 1H), 6.90 (d, J=8.0 Hz, 1H), 6.73 (d, J=8.0 Hz, 1H), 4.94 (m, 1H), 4.40 (s, 1H), 3.30 (t, J=8.6 Hz, 1H), 3.10 (dd, J=15.7, 12.4 Hz, 1H).

Example 6

Preparation of Intermediate Compound 7

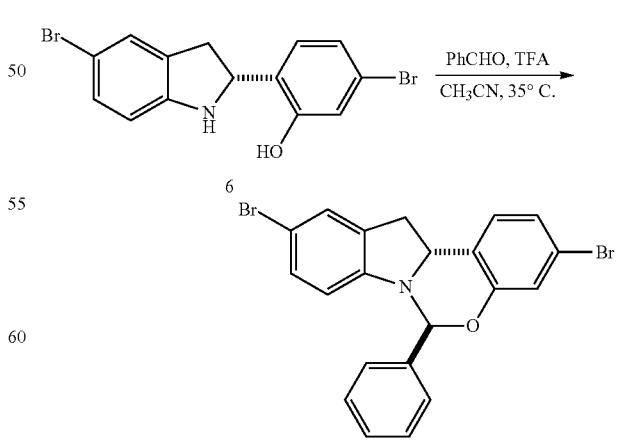

To a suspension of 6 (29.0 g., 79.0 mmol), benzaldehyde (11.15 mL, 110 mmol, 1.4 eq) in acetonitrile (116 mL, 4 vol) in a stirred flask under nitrogen was added TFA (0.303 mL, 0.05 eq) at 20-25° C. The resulting solution was heated to 30-35° C. for 3 hours during which time crystallization of the product was observed. The slurry was cooled to 20-25° C. and held at this temperature for 1 hour. A 5% aqueous sodium bicarbonate solution (13.2 mL, 0.1 eq) was added to the batch followed by a slow addition of water (58 mL). After agitating at 20-25° C. for another 3 hours, the batch was filtered and washed with 87 mL (3 vol) acetonitrile:water (2:1) followed by 58 mL (2 vol) of water. The resulting solid was dried under a nitrogen sweep, providing 7 as a white solid (33.4 g., 73.1 mmol, 93% yield). $^1$H NMR (CDCl$_3$, 400 MHz): δ=7.58 (m, 2H), 7.40-7.36 (m, 4H), 7.23 (s, 1H), 7.08 (d, J=2.0 Hz, 1H), 6.98 (dd, J=8.2, 2.0 Hz, 1H), 6.82 (m, 2H), 6.76 (s, 1H), 4.71 (d, J=8.9 Hz, 1H), 3.52 (dd, J=15.7, 8.9 Hz, 1H), 3.12 (d, J=15.7 Hz, 1H).

Example 7

Preparation of Intermediate Compound 8

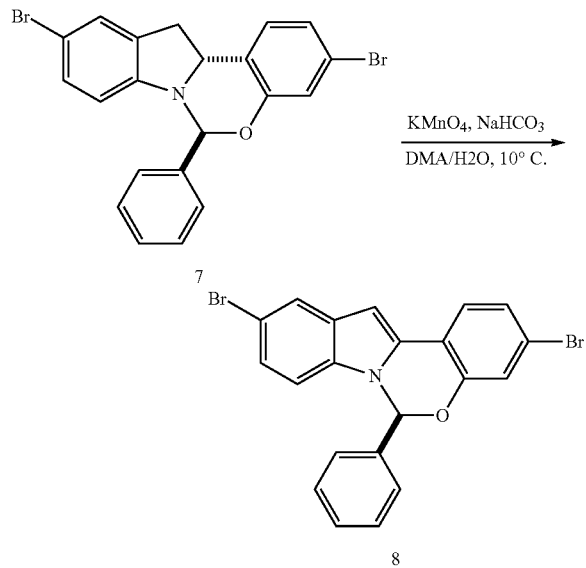

To a round bottom flask was charged 7 (40 g., 106 mmol), NaHCO$_3$ (26.8 g., 3.0 eq, 319 mmol) and DMA (400 mL, 10 vol). The batch was cooled to 10° C. and KMnO$_4$ (32 g., 1.91 eq, 202 mmol) was added followed by a slow addition of water (100 mL, 2.5 vol) while maintaining the batch temperature below 15° C. The reaction was stirred at 10° C. overnight, at which time the reaction was complete. Ethyl acetate (800 mL, 20 vol) was then added and the batch was warmed to 20-25° C. and held at this temperature for 1 hour. A fresh solution of NaHSO3 (24.3 g., 2.2 eq, 234 mmol) in water (400 mL, 10 vol) was slowly added while maintaining the batch temperature below 30° C. After being stirred at 20-25° C. for 1 hour, the batch was transferred to a separatory funnel where the layers were cut. The bottom layer was back extracted with ethyl acetate (400 mL, 10 vol). The combined ethyl acetate fractions were washed with 10% brine 3 times (200 mL, 5 vol each time). ethyl acetate was replaced with isopropanol using vacuum distillation at <50° C. until ethyl acetate was <1% by proton NMR, then crystallized from isopropanol (400 mL, 10 vol) and water (400 mL, 10 vol) at 20-25° C. Once the loss of product in the supernatant was less than 1.0 mg/ml by LC assay (typically 2-3 hours), the batch was filtered and washed with 4 vol of isopropanol:water (1:1). The wet cake was dried at 60-70° C. in a vacuum oven with nitrogen purge overnight to provide 8 as an off-white crystalline solid (40.2 g, 88 mmol, 83% yield, 99% ee). $^1$H NMR (CDCl$_3$, 400 MHz): δ=7.81 (d, J=1.8 Hz, 1H), 7.51 (d, J=8.1 Hz, 1H), 7.37-7.28 (m, 3H), 7.21-7.17 (m, 3H), 7.11-7.08 (m, 3H), 6.85 (s, 1H), 6.70 (d, J=8.8 Hz, 1H), 6.90 (d, J=8.0 Hz, 1H), 6.73 (d, J=8.0 Hz, 1H), 4.94 (m, 1H), 4.40 (s, 1H), 3.30 (t, J=8.6 Hz, 1H), 3.10 (dd, J=15.7, 12.4 Hz, 1H).

Example 8

Preparation of Intermediate Compound 10

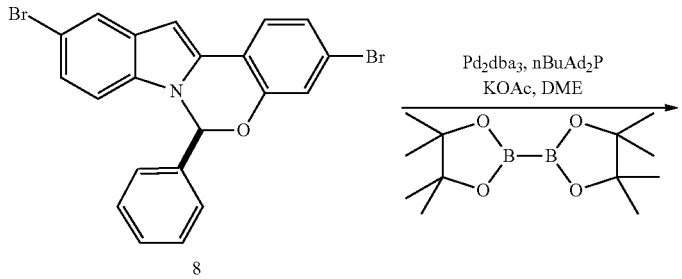

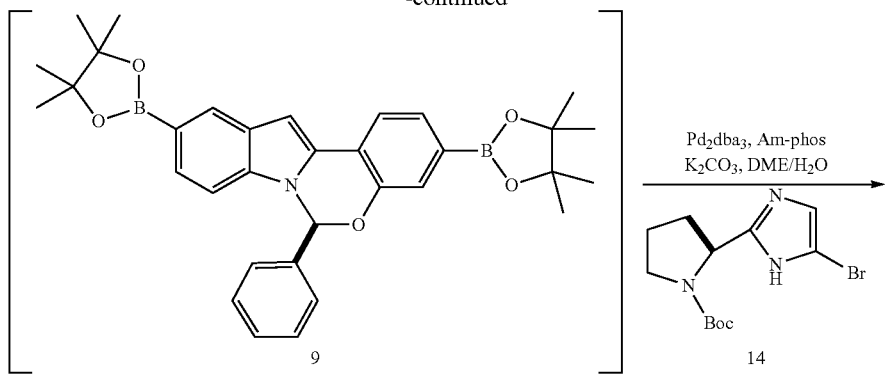

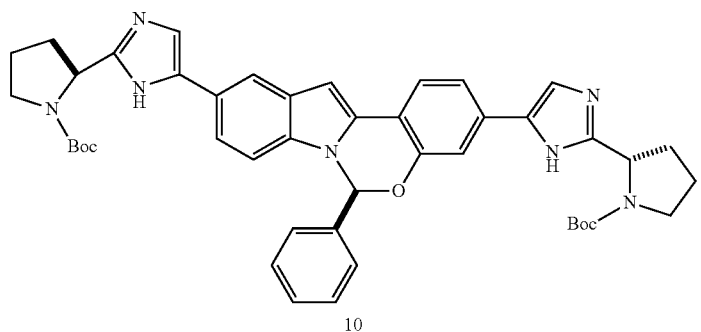

To a 75 L round bottomed flask equipped with an overhead stirrer and a nitrogen inlet was charged 32 L DME, which was degassed with nitrogen. Compound 8 (1.92 kg, 4.22 mol), B(pin)$_2$ (2.36 kg, 9.28 mol) and potassium acetate (2.07 kg, 21.1 mol) were charged to the flask as solids, and the flask was further purged with nitrogen.

To a 3-neck 12 L round bottomed flask equipped with an overhead stirrer and a nitrogen inlet was charged 4 L methanol-THF which was then degassed with nitrogen. Pd$_2$dba$_3$ (0.039 kg, 0.042 mol) and CataCXium A (0.060 kg, 0.169 mol) were then charged as solids, and the mixture aged under nitrogen for 30 mins, formed dark red solution. The catalyst solution was transferred to the 75 L flask under nitrogen, and the solution was heated to reflux (80-83° C.) and aged for 4 hours. The reaction was cooled down to room temperature, at which time 10 L degassed water was charged the reaction flask.

At this time, potassium carbonate (3.50 kg, 25.3 mol) and 14 (3.03 kg, 9.49 mol), were charged under nitrogen.

To a 3-neck 12 L round bottom flask equipped with an overhead stirrer and a nitrogen inlet was charged 4 L methanol-THF which was then degassed with nitrogen. Pd$_2$dba$_3$ (0.068 kg, 0.074 mol) and Am-Phos (0.078 kg, 0.295 mol) were charged as solids, and the solution aged at room temperature for 30 minutes. The solution was then transferred to the 75 L reaction flask under nitrogen. The reaction was heated to reflux (approximately 77° C.) under nitrogen and aged for 16 hours. The reaction was then cooled to room temperature, and transferred to a 170 L cylindrical vessel along with 20 L ethyl acetate and 30 L water. The mixture was stirred for 30 mins, and the aqueous layer was cut.

To the organic layer was added 20 L 20 wt % aqueous glycolic acid and the mixture was aged at room temperature for 30 minutes with stirring. The aqueous layer was separated and retained, and the organics extracted again with 10 L 20 wt % glycolic acid. The aqueous cuts were combined, and 20 L methanol-THF was added. The mixture was basified to a pH of 9 using 28% ammonium hydroxide. The aqueous layer was then cut and discarded. The organic layer was washed with 10 wt % aqueous Na$_2$SO$_3$ and brine. The organic layer was charged into a 75 L flask, then 1 kg MP-TMT and 600 g Darco-KB was charged, and stirred for 2 hours. The mixture was filtered and washed with 4 L methanol-THF twice.

The solution was concentrated and flushed with toluene, maintaining a 25 L volume and reducing the methanol-THF content below 2% as determined by HNMR. The toluene mixture was heated to 60° C. to a solution, at which time 4-nitrobenzoic acid (1.410 kg, 8.44 mol) was charged as a solid, and the mixture aged 1 hour. The solution was then slowly cooled to room temperature and aged overnight. At this time the slurry was cooled to 5° C. and filtered. The solids were washed with cold toluene (4 L), then dried under nitrogen. Nitro benzoate salt 10 was obtained as a yellow solid (3.80 kg, 82% overall yield). $^1$H NMR (DMSO, 500 MHz): δ=8.32 (dt, 4H, J=9.0, 2.0 Hz), 8.18 (dt, 4H, J=9.0, 2.0 Hz), 7.99 (s, 1H), 7.79 (d, 1H, J=8.0 Hz), 7.71 (s, 1H), 7.54-7.46 (m, 3H), 7.42-7.37 (m, 2H), 7.30-7.27 (m, 4H), 7.08 (s, 1H), 7.01 (m, 2H), 4.82 (m, 2H), 3.55 (br s, 2H), 3.37 (m, 2H), 2.32-2.10 (m, 2H), 2.08-1.83 (m, 6H), 1.41-1.16 (m, 18H).

Example 9

Preparation of Intermediate Compound 11

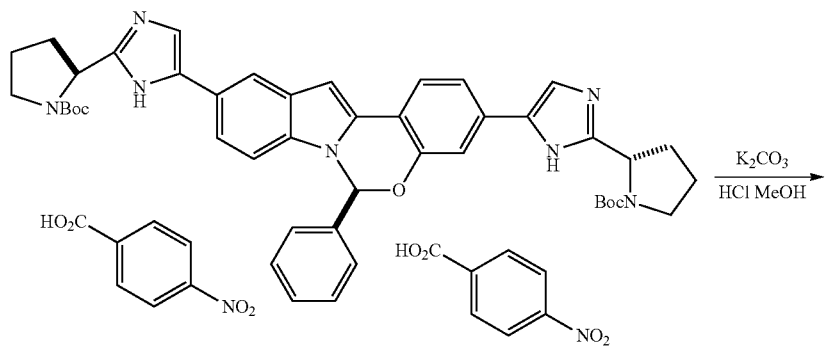

10

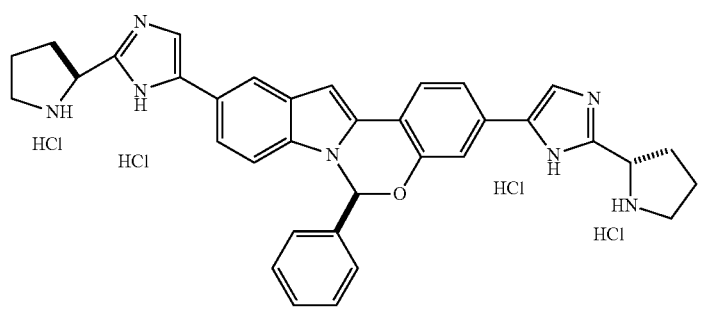

11

A 100 L extractor equipped with overhead stirring was charged with potassium carbonate (2.09 kg, 15.12 mol, 4.46 equiv) and water (48.6 kg, 48.6 L, 13 vol), and was stirred until the aqueous layer was homogenous. The aqueous solution was then divided into a drum containing approximately 7 volumes of the carbonate solution (26.2 L), and three drums containing approximately 2 volumes of the carbonate solution (7.5 L). At this time the 7 volumes (26.2 L) aqueous solution was charged back to the extractor, followed by ethyl acetate (49.8 kg, 55.2 L, 13 vol) and 10 (3.74 kg, 3.39 mol). The resulting slurry was stirred until the biphasic mixture became a clear solution. The aqueous layer was cut and the organics washed three times successively with the 2 vol carbonate solutions, and finally with water (7.48 kg, 7.48 L, 2 vol). The organics were then transferred to a 100 L, 5-necked round bottomed flask equipped with an overhead stirrer and a nitrogen inlet. ethyl acetate was solvent switched to methanol (5 vol, 14.8 kg, 18.7 L) maintaining internal temperature at or below 30° C. during distillation.

Hydrochloric acid (37%, 2.68 kg, 2.23 L, 8.0 equiv) was then charged slowly over 30 minutes maintaining internal temperature below 40° C. At the end of addition the reaction was heated to 45° C., and this temperature was maintained until conversion of the reaction is complete (approximately 4 hours). Over this time the HCl salt (2) of the product should crystallize out of solution. At the end of the reaction, the mixture was cooled to room temperature, acetonitrile (38.2 kg, 48.6 L, 13 vol) was added and the slurry was aged at room temperature for 14 hours or until the solution concentration of 2 was <3 mg/mL.

The slurry was then filtered and washed twice successively with 2 vol (8.49 L) acetonitrile. The wet cake was dried by nitrogen sweep, yielding 2.23 kg 2 (3.13 mol, 92% yield) as a pale yellow solid. $^1$H NMR (DMSO-$d_6$, 500 MHz): δ=8.31 (d, J=0.7 Hz, 1H), 8.21 (s, 1H), 8.19 (s, 1H), 8.05 (d, J=8.0 Hz, 1H), 7.88 (s, 1H), 7.72 (m, 3H), 7.47 (d, J=8.8 Hz, 1H), 7.32 (m, 4H), 7.02 (m, 1H), 5.16 (t, J=8.0 Hz, 1H), 5.06 (t, J=8.0 Hz, 1H), 3.52-3.37 (m, 4H), 2.57-2.47 (m, 5H), 2.24-2.17 (m, 2H), 2.08-1.91 (m, 2H).

Example 10

Preparation of Compound A

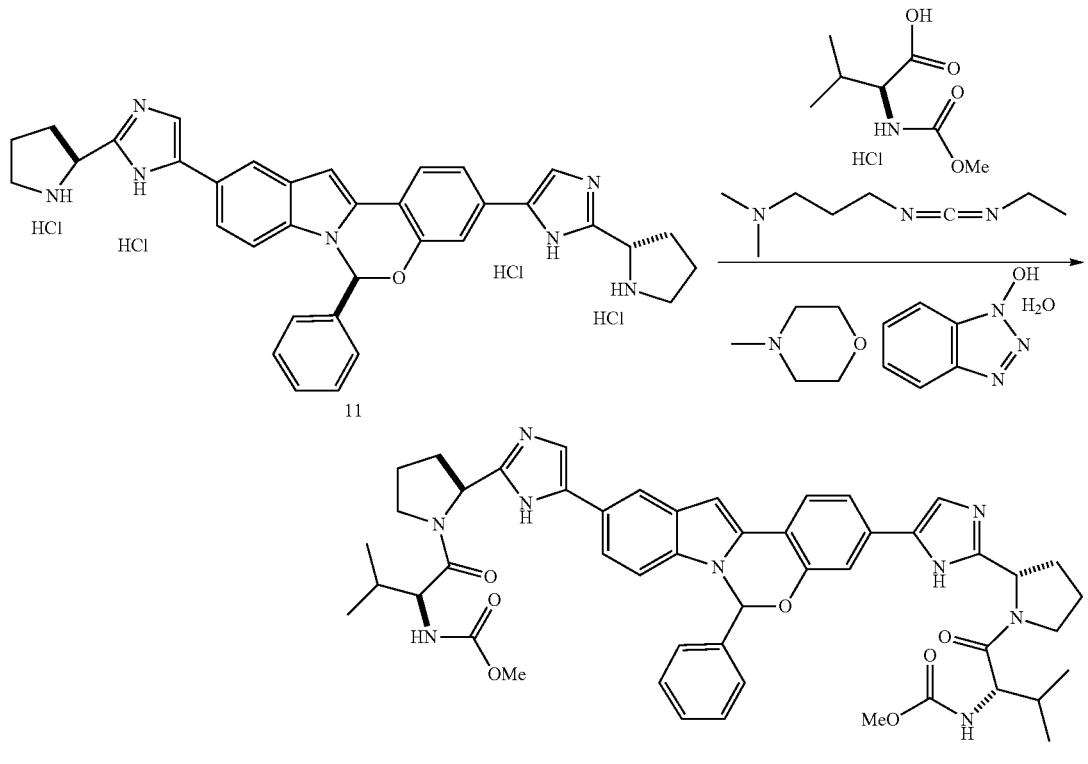

To a 100 L, 5-necked round bottomed flask equipped with an overhead stirrer and a nitrogen inlet was charged acetonitrile (17.5 kg, 22.3 L, 10 vol) and 11 (2.23 kg, 3.13 mol). The mixture was cooled with an ice bath targeting an internal temperature below 10° C. At this time N-Moc-Valine (1.20 kg, 6.88 mol, 2.2 equiv) was charged followed by N-methyl morpholine (2.21 kg, 2.40 L, 21.9 mol, 7 equiv) slowly via additional funnel over 30 minutes maintaining internal temperature below 20° C. Then HOBt hydrate (239 g., 1.56 mol, 0.5 equiv) was added as a solid charge, followed by EDC-HCl (1.32 kg, 6.88 mol, 2.2 equiv). The ice bath was removed and the solution warmed to room temperature and aged overnight.

Upon confirmation of target conversion, the reaction was diluted with ethyl acetate (20.1 kg, 22.3 L, 10 vol) and transferred to a 100 L extractor equipped with overhead stirring. The organics were washed successively with 2M ammonium chloride (8.84 L, 4 vol), 10 wt % NaHCO$_3$ (11.0 L, 5 vol), 10 wt % Na$_2$CO$_3$ (11.0 L, 5 vol) and water (6.6 L, 3 vol). The organics were then transferred to a 50 L round bottomed flask via tubing equipped with an in-line filter for batch concentration. The organics were concentrated to approximately 13.2 L or 6 volumes and solvent switched to ethanol maintaining internal temperature at or below 35° C. during distillation.

At this time the mixture was seeded with 0.5 wt % crystalline 3 and stirred for 60 hours. The target mother liquor concentration of this solution is 6 mg/mL. If concentration exceeds this then slowly cool the slurry at a rate of 2° C. per hour until the target concentration is met. The slurry was then filtered and slurry washed twice with 6.6 L (3.0 vol) ethanol. The wet cake was dried under nitrogen stream, to provide Compound A (2.20 kg, 2.50 mol) as a white solid. $^1$H NMR (DMSO-d$_6$, 600 MHz): δ=8.13 (s, 1H), 8.10 (s, 1H), 8.07 (d, J=8.4 Hz, 1H), 7.99 (s, 1H), 7.89 (s, 1H), 7.56-7.54 (m, 3H), 7.52 (d, J=8.7 Hz, 1H), 7.35 (s, 1H), 7.31-7.27 (m, 5H), 6.97 (m, 2H), 5.16 (t, J=7.3 Hz, 1H), 5.12 (t, J=7.3 Hz, 1H), 4.15-4.11 (m, 2H), 3.91-3.80 (m, 4H), 3.55 (s, 3H), 3.54 (s, 3H), 2.45-2.36 (m, 2H), 2.02-1.98 (m, 8H), 0.85 (d, J=6.8 Hz, 3H), 0.82 (d, J=6.8 Hz, 3H), 0.80 (d, J=6.8 Hz, 3H), 0.77 (d, J=6.8 Hz, 3H).

Example 11

Preparation of Intermediate Compound 13

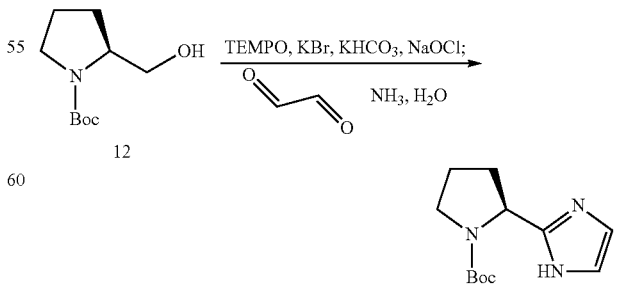

A 100 L, 5-necked round bottomed flask equipped with an overhead stirrer and a nitrogen inlet was charged with alcohol 12 (3.80 kg, 18.88 mol) and dichloromethane (6.0 vol, 30.2 kg, 22.8 L). The solution was cooled to an internal temperature below 5° C. (target range 0-5° C.). A solution of potassium bromide (449 g, 3.78 mol, 0.2 equiv) in water (1.2 vol, 4.56 kg, 4.56 L) was added as a single charge. TEMPO (59.0 g., 0.378 mol, 0.02 equiv) was then added as a single solid charge. Potassium bicarbonate (3.78 kg, 37.8 mol, 2.0 equiv) was added as a water (6 vol, 22.8 kg, 22.8 L) solution over 10 minutes. After 10 minutes stirring, 10 wt % sodium hypochlorite (14.06 kg, 11.65 L, 1.0 equiv) was added over 1 hour maintaining internal temperature between 0-5° C. After 30 minutes stirring the organic layer was assayed for conversion of alcohol 12.

When the reaction is judged to be complete, a solution of sodium thiosulfate (1.49 kg, 9.44 mol, 0.5 equiv) is added as a water (2 vol, 7.60 kg, 7.60 L) solution over 15 minutes with stirring. The mixture was then allowed to warm to room temperature and was then concentrated in vacuo. The aqueous layer is extracted with dichloromethane (3 vol, 11.4 L, 15.1 kg), and the organics combined (note: there may be precipitated salts in the organics at this point). The organics were then washed with water (5 vol, 19.0 L, 19.0 kg), and then solvent switched to acetonitrile (5 vol, 14.8 kg, 18.8 L) while maintaining internal temperature at or below 30° C. during distillation.

The acetonitrile solution was cooled to an internal temperature below 5° C. (target range 0-5° C.). NH$_4$OH (10.5 L, 9.45 kg, 75 mol, 28% aqueous solution, 4 equiv) was added over 1 hour to the acetonitrile solution maintaining internal temperature between 0-5° C. Glyoxal (3.02 L, 3.83 kg, 26.4 mol 40% aqueous solution, 1.4 equiv) was added over 1 hour maintaining internal temperature between 0-5° C. and the reaction stirred at ambient temperature for 19 hours. At this time HPLC analysis shows <2% residual starting material by weight (note: if residual aldehyde is present a further charge of 0.2 eq. glyoxal will drive conversion). The reaction was diluted with 10 vol ethyl acetate (33.9 kg, 37.6 L), and washed with 2 volumes 20 wt % NaCl (7.5 L). The organics were then successively washed with 3 volumes 20 wt % NaCl (11.3 L) and 3 volumes water (11.3 L). The organics were solvent switched to approximately 4 volumes (15.0 L, 13.0 kg) Toluene, then n-heptane (6 volumes, 15.4 kg, 22.6 L) was slowly added over 1 hour to precipitate out compound 13 which was stirred until the solution concentration of 13 was <8 mg/mL (if concentration is higher, further heptane charge should be added until the target concentration is reached). The slurry was filtered, washed with 3 volumes 40% Toluene/Heptane, and dried to provide compound 13 (as a mixture of rotamers) as a white solid (3.1 kg, 70% yield). $^1$H NMR (DMSO, 400 MHz): 11.64 (br s, 1H), 6.85 (br s, 1H), 4.80-4.73 (m, 1H), 3.48 (br s, 1H), 3.32 (m, 1H), 2.50 (m, 1H), 2.23-1.73 (m, 4H), 1.39/1.15 (s, 9H).

Example 12

Preparation of Intermediate Compound 14

Into a clean, 100 L flask equipped with an overhead stirrer was charged compound 13 (5.32 kg, 19.1 mol) and methanol (26.6 L). Under a nitrogen atmosphere, the mixture was stirred at 20° C. for about 45 minutes to ensure all solids were dissolved. The solution was cooled to a temperature between −20 and −10° C. N-bromosuccinimide (7.76 kg, 43.5 mol, 2.2 equiv) was added directly to the vessel in portions while maintaining a batch temperature between −20 and −10° C. Water (8 L, ambient temperature) was added to the reaction mixture. The batch temperature increased to about 15-20° C. An additional 8.5 L water was added over about 30 minutes. During this second charge of water, product crystallization had initiated. The batch was held at a temperature range of 15-20° C. for 30 minutes. A further charge of water (27.5 L) was then added over 1.5 hours. The solids were filtered and the wet cake was washed with 10 volumes of aqueous methanol (5:8 ratio of methanol:H$_2$O).

The filtered solids were then charged into a 100 L round bottom flask equipped with an overhead turbine stirrer, baffle, nitrogen inlet, and thermocouple. To this flask was charged 27.2 L methanol, and then 5.44 L water slowly. After 20 minutes, 4.83 kg EDTA was added followed by 4.60 L NH$_4$OH over 5 minutes, and a clear solution formed, and the temperature maintained <30° C. At this time, 1.0 eq (0.901 kg) Zn dust was added in 100-200 g portions over the course of 2 hours, maintaining the temperature at 30° C. After a further 3 hours aging, an additional 0.1 equiv Zn dust was added (90.1 g.). HPLC showed 91% conversion at this time. After overnight aging, a further 0.2 equiv Zn dust (180.2 g.) was charged over the course of 4 hours, and after an additional 2 hours of aging, the reaction was complete.

The light tan solution was decanted with a pump from the remaining particles of Zn and transferred into a 170 L extractor pre-charged with 4.0 L ethyl acetate, 16.3 L 30% (0.87 M) aqueous Na$_4$EDTA and 27.2 L 20% aq NaCl. 44 L ethyl acetate was used to wash out the reaction flask and transferred into the extractor. The aqueous layer was cut, and the organics washed successively with 38 L 20% aq NaCl, 42 L 15% (1.15M) aqueous KH$_2$PO$_4$, 42 L 15% (1.15M) aqueous KH$_2$PO$_4$, and finally 27 L water.

The organic layer was concentrated in a 72 L flask to a 20 L volume (spontaneously crystallized), and solvent switched with 20 L toluene to an 11 L total volume at 30° C. to 40° C. 16 L n-heptane was added over 1 h while the temperature gradually decreased from 40° C. to 25° C. The slurry was further cooled to 20° C. The slurry was filtered after 1 h agitation at 20° C., and the solids dried in the filter pot under a nitrogen stream and ambient temperature to provide compound 14 (3.70 kg, 61% yield, >99.9% ee) as large, pale yellow crystals. $^1$H NMR (400 MHz, CDCl$_3$): δ=6.89 (s, 1H), 4.88 (dd, J=7.8, 2.7 Hz, 1H), 3.79 (m, 2H), 2.87 (m, 1H), 2.10 (m, 1H), 1.92 (m, 1H), 1.47 (s, 9H).

Example 13

Preparation of Intermediate Compounds 16 and 17

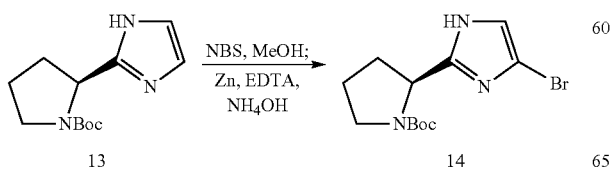

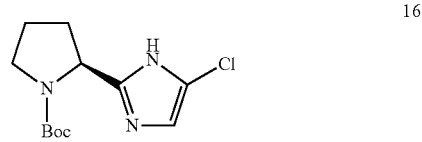

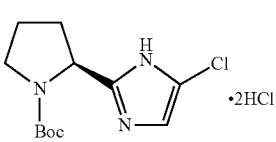

Step A—Preparation of Intermediate Compound 15

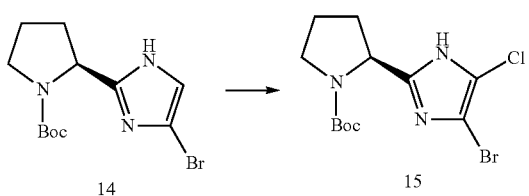 [SMILES: CC(C)(C)OC(=O)N1CCC[C@H]1c1nc(Br)c[nH]1 ; CC(C)(C)OC(=O)N1CCC[C@H]1c1nc(Br)c(Cl)[nH]1]

To a solution of (S)-tert-butyl 2-(4-bromo-1H-imidazol-2-yl)pyrrolidine-1-carboxylate (14, 20.0 g, 63.3 mmol) in MeOH (100 mL) was added NCS (9.29 g, 69.6 mmol) and the resulting reaction was allowed to stir at room temperature for about 15 hours. The reaction mixture was then concentrated in vacuo and triturated with water. The crystals obtained were filtered and washed with a mixture of MeOH and water (9:1 v/v) and allowed to dry in an oven at 40° C. for about 15 hours to provide compound 15 (21.3 g, 96%). $^1$H NMR for a mixture of two rotamers (~6:4 ratio: NMR reported as 6:4 mixture) (400 MHz, DMSO-$d_6$) δ 13.02 (br s, 1 H), 4.67 (br s, 0.4 H), 4.59 (br s, 0.6 H), 3.55-43 (m, 1 H), 3.48-3.44 (m, 1 H), 2.28-2.16 (m, 1 H), 2.00-1.77 (m, 3 H), 1.38 (s, 3.6 H), 1.18 (s, 5.4 H). $^{13}$C NMR for the major rotamer (100 MHz, DMSO-$d_6$) δ 153.0, 150.3, 126.4, 94.0, 78.5, 55.2, 46.2, 33.0, 27.8, 22.9. $^{13}$C NMR for the minor rotamer (100 MHz, DMSO-$d_6$) δ 153.5, 149.8, 126.4, 94.4, 78.8, 54.8, 46.5, 31.9, 28.1, 23.6. MP 168-170° C. Calcd. exact mass for $C_{12}H_{17}BrClN_3O_2$ [M+H]$^+$: 349.0271; found: 350.0320.

Step B—Preparation of Intermediate Compound 16

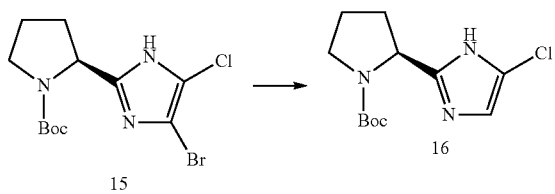 [SMILES: CC(C)(C)OC(=O)N1CCC[C@H]1c1nc(Br)c(Cl)[nH]1 ; CC(C)(C)OC(=O)N1CCC[C@H]1c1ncc(Cl)[nH]1]

To a solution of compound 15 (9.00 g, 25.7 mmol) in MeOH (30 mL) was added water (9 mL), EDTA (9.0 g, 1.2 equiv), aqueous ammonium hydroxide (28%, 9.5 ml, 2.7 equiv) and Zn dust (5.0 g, 3.0 equiv). The resulting reaction was heated to 45° C. and allowed to stir at this temperature for 7 hours. The remaining Zn dust was filtered off and the filtrate was mixed with EtOAc (50 mL) and brine (50 mL). The organic layer was separated and washed with brine (30 mL) followed by aqueous citric acid solution (0.5%, 54 mL). The solvent was removed in vacuo at 50° C. and the resulting residue was taken up in MeOH (27 mL). Water (90 ml) was added slowly over 1 hour at room temperature. The solids formed were collected by filtration and dried in a vacuum oven for about 15 hours at 60° C. to provide compound 16 (5.5 g, 79%). $^1$H NMR for a mixture of two rotamers (~6:4 ratio: NMR reported as 6:4 mixture) (400 MHz, DMSO-$d_6$) δ 12.10 (br s, 0.6 H), 12.05 (br s, 0.4 H), 7.05 (br s, 0.6 H), 7.00 (br s, 0.4 H), 4.70 (br s, 0.4 H), 4.65 (br s, 0.6 H), 3.49 (br, 1 H), 3.30 (m, 1 H), 2.30-2.10 (m, 1 H), 2.00-1.70 (m, 3 H), 1.38 (s, 3.6 H), 1.18 (s, 5.4 H). $^{13}$C NMR for the major rotamer (100 MHz, DMSO-$d_6$) δ 153.7, 149.6, 126.9, 111.6, 78.7, 55.5, 46.7, 33.6, 28.3, 23.4. $^{13}$C NMR for the minor rotamer (100 MHz, DMSO-$d_6$) δ 154.2, 148.9, 126.9, 112.2, 79.1, 54.9, 46.9, 32.1, 28.6, 24.2. MP 144-146° C. Calcd. exact mass for $C_{12}H_{18}ClN_3O_2$ [M+H]$^+$: 272.1166; found: 272.1182.

Step C—Preparation of Intermediate Compound 17 (Compound 16 Dihydrochloride Salt)

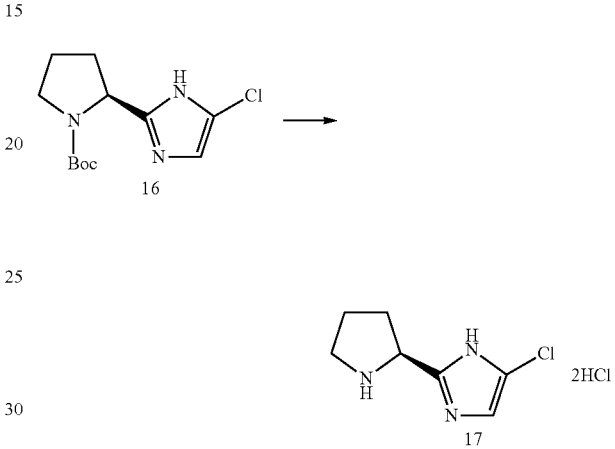

A mixture of compound 16 (2.00 g, 7.36 mmol) and HCl solution in isopropanol (5-6 N, 10 mL) was allowed to stir at room temperature for about 15 hours. The suspension was then heated to 35° C. and allowed to stir at this temperature for an additional 2 hours. The resulting suspension was filtered and washed with isopropanol (3 mL) and the collected solids were dried in a vacuum oven for 6 hours at 60° C. to provide compound 17 (the dihydrochloride salt of 16) (1.62 g, 90%). $^1$H NMR (400 MHz, DMSO-$d_6$) δ 13.40 (br s, 2 H), 10.50 (br s, 1 H), 9.30 (br s, 1 H), 7.35 (s, 1 H), 4.65 (m, 1 H), 3.26 (m, 2 H), 2.30 (m, 1 H), 2.25 (m, 1 H), 2.15 (m, 1 H), 1.96 (m, 1 H). $^{13}$C NMR (100 MHz, DMSO-$d_6$) δ 142.3, 126.8, 114.8, 55.0, 45.1, 30.1, 23.8. MP 189-193° C. Calcd. exact mass for $C_7H_{10}ClN_3$[M+H]$^+$: 172.0642; found: 172.0652.

Example 14

Preparation of Intermediate Compound 18

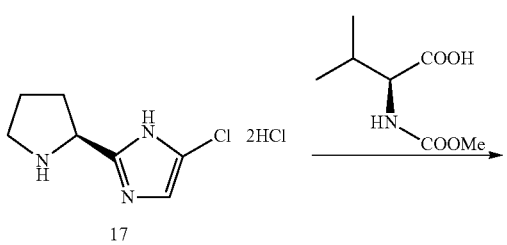

-continued

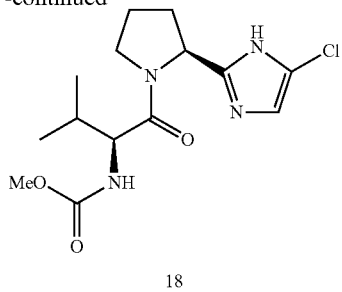

18

To a suspension of compound 17 (1.2 g, 4.9 mmol) in THF (20 mL) was added (S)-2-((methoxycarbonyl)amino)-3-methylbutanoic acid (0.86 g, 4.9 mmol), diisopropylethylamine (1.9 g), 1-hydroxylbenzotriazole monohydrate (0.7 g) and EDCI hydrochloride salt (1.1 g). The resulting reaction was allowed to stir at room temperature for 2 hours. Ethyl acetate (20 mL) and aqueous sodium bicarbonate solution (10%, 20 mL) were then added to the reaction mixture and the organic layer was separated and washed sequentially with aqueous sodium bicarbonate solution (10%, 2×20 mL) and water (20 mL). The organic layer was concentrated in vacuo and the resulting residue was taken up in ethyl acetate (10 mL). Hexanes (10 mL) was added slowly to the ethyl acetate solution over 1 hour at room temperature, resulting in precipitation of colorless solids. The solids were collected by filtration and dried in a vacuum oven at 60° C. for about 15 hours to provide compound 18 (1.15 g, 71%). $^1$H NMR (400 MHz, DMSO-d$_6$) δ 12.00 (br s, 1 H), 7.35 (d, J=8.3 Hz, 1 H), 7.05 (s, 1 H), 4.92 (br s, 1 H), 4.02 (t, J=8.2 Hz, 1 H), 3.30-3.10 (m, 2 H), 3.49 (s, 3 H), 2.10 (br s, 2 H), 2.00-1.80 (br s, 2 H), 0.85 (m, 1 H), 0.80 (d, J=6.4 Hz, 6 H). $^{13}$C NMR (100 MHz, DMSO-d$_6$) δ 170.9, 157.3, 148.4, 126.8, 112.1, 58.4, 54.5, 51.9, 47.2, 31.2, 30.2, 24.7, 19.4, 18.8. MP 147-151° C. Calcd. exact mass for C$_{14}$H$_{21}$ClN$_4$O$_3$ [M+H]$^+$: 329.1380; found: 329.1390.

Example 15

Alternate Preparation of Intermediate Compound 10

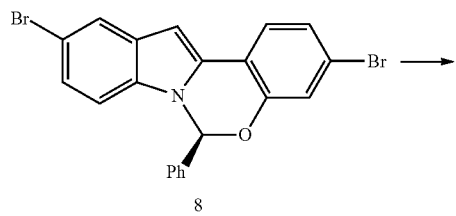

8

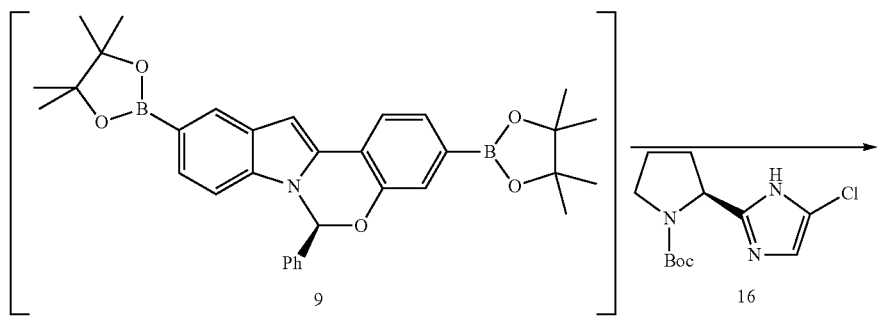

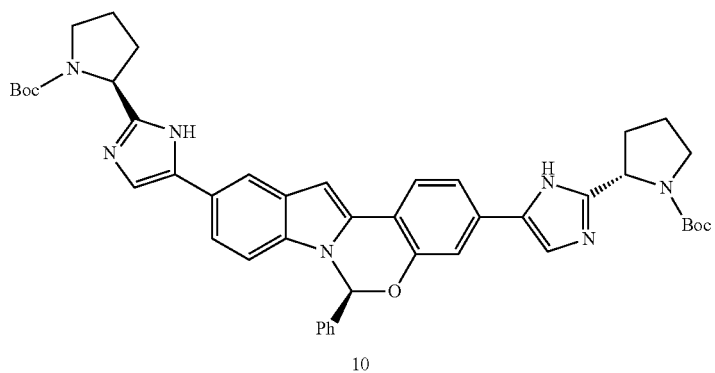

10

Compound 9 was prepared from compound 8, as described in Example 8. Compound 9 was then reacted with compound 16 in the presence of 2 mol % Pd(OAc)$_2$, 4 mol % Xphos, 8 equiv. of 1.5 M K$_3$PO$_4$ in DME at 100° C. for 20 hours to provide Compound 10.

Example 16

Alternate Preparation of Compound A

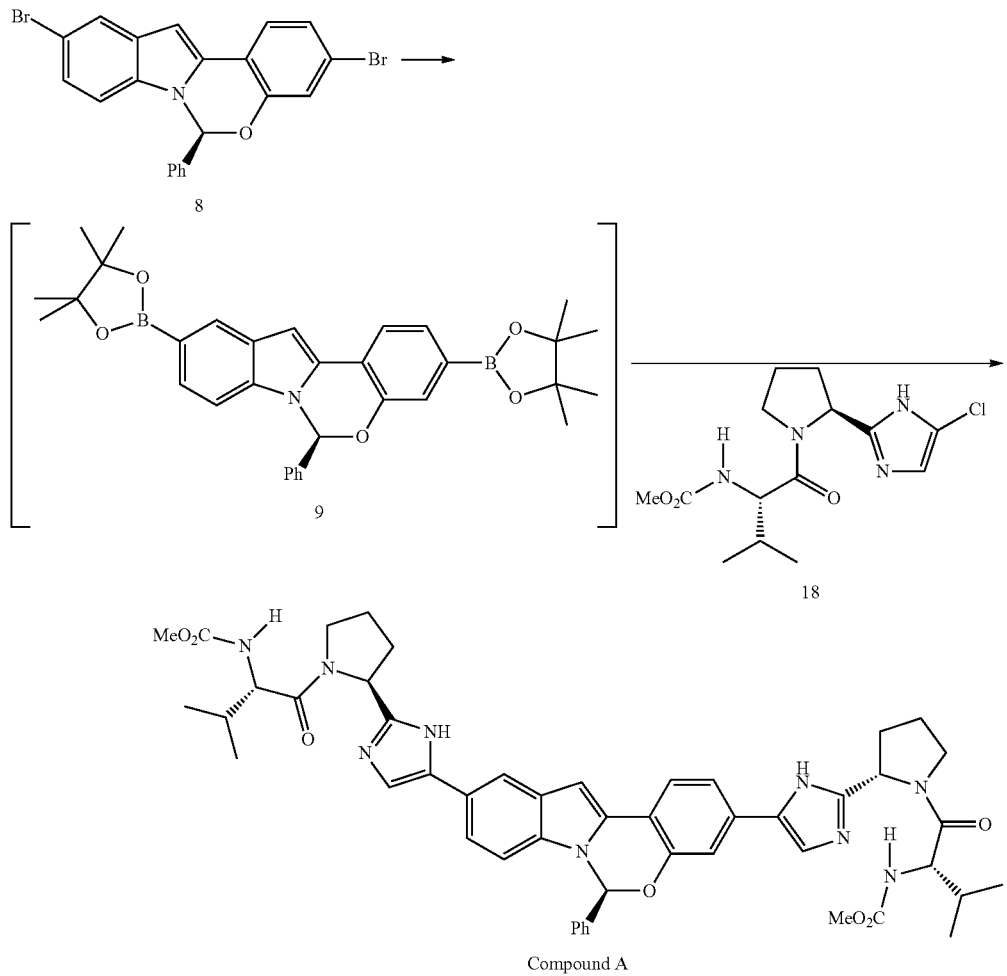

Compound 9 was prepared from compound 8, as described in Example 8. Compound 9 was then reacted with compound 18 in the presence of 2 mol % Pd(OAc)$_2$, 4 mol % Xphos, 8 equiv. of 1.5 M K$_3$CO$_3$ in DME at 100° C. for 20 hours to provide Compound A.

While the foregoing specification teaches the principles of the present invention, with examples provided for the purpose of illustration, the practice of the invention encompasses all of the usual variations, adaptations and/or modifications that come within the scope of the following claims. All publications, patents and patent applications cited herein are incorporated by reference in their entirety into the disclosure.

What is claimed is:

1. A process for preparing a compound of Formula I:

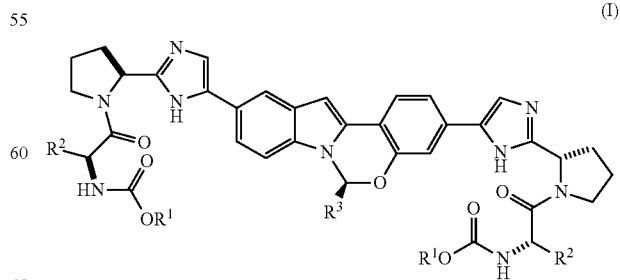

and pharmaceutically acceptable salts thereof, wherein said process comprises:

(A) (i) contacting the compound of Formula VI with bis(pinacoloato)diboron in the presence of an acetate or pivalate base, a transition metal catalyst, and optionally in the presence of a phosphorus ligand source, in a mixture of water and an organic solvent E, to provide an intermediate compound of Formula VII:

(VII)

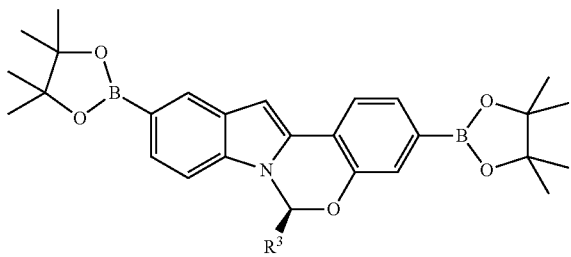

then (ii) contacting the intermediate compound of formula VII with a compound of formula VIIb (VIIb)

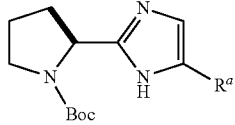

in the presence of a carbonate, acetate or pivalate base and a transition metal catalyst, and optionally in the presence of a phosphorus ligand source, in said mixture of water and organic solvent E, to provide a compound of formula VIII:

(VIII)

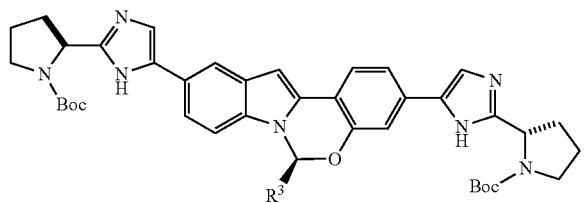

wherein organic solvent E is selected from dimethylacetamide, toluene, acetonitrile, N,N-dimethylformamide, tetrahydrofuran, 2-methyl tetrahydrofuran, cyclopentyl methyl ether, isopropanol, ethanol, ethyl acetate, isopropyl acetate and dimethoxyethane; and (B) (i) contacting the di-p-nitrobenzoate salt of the compound of Formula VIII with an inorganic base, in an organic solvent F, for a time sufficient to remove the Boc protecting groups from the compound of Formula VIII, then (ii) contacting the deprotected compound in situ with HCl to provide a compound of Formula IX:

(IX)

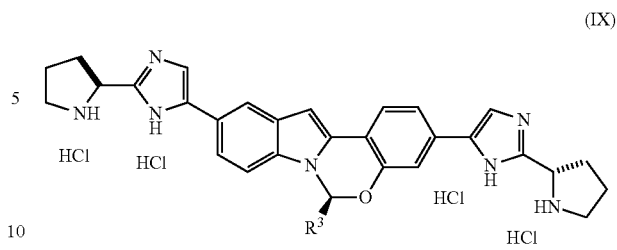

wherein organic solvent F is selected from methanol, acetonitrile, tetrahydrofuran, 2-methyl tetrahydrofuran, ethanol, isopropanol and toluene; and (C) contacting the compound of Formula IX with: (i) an additive selected from 2-hydroxypyridine-N-oxide, N-hydroxysuccinimide, HOBt and pyridine, and (ii) a non-nucleophilic base) in the presence of (i) a compound of formula Xa:

(Xa)

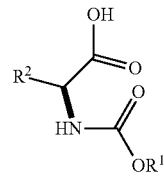

and (ii) an amide coupling reagent in an organic solvent G to provide a compound of Formula I:

(I)

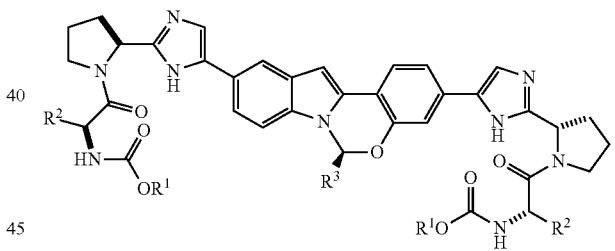

wherein organic solvent G is selected from tetrahydrofuran, N,N-dimethylformamide, dimethylacetamide, N-methylpyrrolidinone and dimethylsulfoxide; and wherein each occurrence of $R^1$ is independently $C_1$-$C_6$ alkyl, $C_3$-$C_7$ cycloalkyl or $C_6$-$C_{10}$ aryl;

each occurrence of $R^2$ is independently $C_1$-$C_6$ alkyl, $C_3$-$C_7$ cycloalkyl, 3 to 7-membered monocyclic heterocycloalkyl or $C_6$-$C_{10}$ aryl;

$R^3$ is $C_1$-$C_6$ alkyl, $C_3$-$C_7$ cycloalkyl, $C_6$-$C_{10}$ aryl, 5 or 6-membered monocyclic heteroaryl or 9 or 10-membered bicyclic heteroaryl, wherein said $C_3$-$C_7$ cycloalkyl group, said $C_6$-$C_{10}$ aryl group, said 5 or 6-membered monocyclic heteroaryl group or said 9 or 10-membered bicyclic heteroaryl group can be optionally substituted with up to three groups, each independently selected from $C_1$-$C_6$ alkyl and $C_3$-$C_7$ cycloalkyl; and $R^a$ is Br, Cl or I.

2. The process according to claim 1, wherein:

Step A, part (i) is conducted at a temperature in a range of from about 40° C. to about 110° C.;

the organic solvent employed in step A, part (i) is N,N-dimethylformamide;

the acetate or pivalate base employed in Step A, part (i) is selected from NaOAc, CsOAc, KOPiv, NaOPiv and potassium acetate;

the transition metal catalyst employed in Step A, part (i) is selected from $Pd_2dba_3$, $Pd(OAc)_2$ and $PdCl_2$;

the optional phosphine ligand employed in Step A, part (i) is selected from N-Bu(Ad)$_2$P, Am-phos, n-BuP(t-Bu)$_2$-HBF$_4$, XPhos, SPhos, BrettPhos, DTBPF, PCy$_3$ and P(t-Bu)$_3$;

Step A, part (ii) is conducted at a temperature in a range of from about 40° C. to about 110° C.;

the organic solvent employed in step A, part (ii) is N,N-dimethylformamide;

the carbonate, acetate or pivalate base employed in Step A, part (ii) is selected from $K_2CO_3$, NaOAc, CsOAc, KOPiv, NaOPiv and potassium acetate;

the transition metal catalyst employed in Step A part (ii) is selected from $Pd_2dba_3$, $Pd(OAc)_2$ and $PdCl_2$;

the optional phosphine ligand employed in Step A, part (ii) is selected from N-Bu(Ad)$_2$P, Am-phos, n-BuP(t-Bu)$_2$-HBF$_4$, XPhos, SPhos, BrettPhos, DTBPF, PCy$_3$ and P(t-Bu)$_3$;

Step B, part (i) is conducted at a temperature in a range of from about 0° C. to about 60° C.;

the organic solvent employed in step B is N,N-dimethylformamide;

the inorganic base employed in step B is selected from a carbonate base, a phosponate base or an alkali metal hydroxide base;

Step B, part (ii) is conducted at a temperature in a range of from about 20° C. to about 60° C.;

Step C is conducted at a temperature in a range of from about −10° C. to about 60° C.;

the organic solvent employed in step C is N,N-dimethylformamide;

the non-nucleophilic base employed in step C is selected from (N-methylmorpholine, triethylamine, diisopropylethylamine and pyridine;

the amide coupling reagent employed in step C is selected from DCC, HATU, T3P and N-(3-dimethylaminopropyl)-N'-ethylcarbodiimide hydrochloride.

3. The process according to claim 1, wherein each occurrence of $R^1$ and $R^2$ is independently $C_1$-$C_6$ alkyl and $R^3$ is 5 or 6-membered heteroaryl or $C_6$-$C_{10}$ aryl, wherein $R^3$ can be optionally substituted with a group selected from $C_1$-$C_6$ alkyl and $C_3$-$C_7$ cycloalkyl.

4. The process according to claim 1, wherein:

Step A, part (i) is conducted at a temperature in a range of from about 70° C. to about 90° C.;

the organic solvent employed in step A, part (i) is a mixture of DME and water;

the acetate or pivalate base employed in Step A, part (i) is selected from NaOAc, CsOAc and potassium acetate;

the transition metal catalyst employed in Step A part (i) is $Pd_2dba_3$;

the optional phosphine ligand employed in Step A, part (i) is N-Bu(Ad)$_2$P;

Step A, part (ii) is conducted at a temperature in a range of from about 70° C. to about 90° C.;

the organic solvent employed in step A, part (ii) is a mixture of DME and water;

the carbonate, acetate or pivalate base employed in Step A, part (ii) is $Na_2CO_3$ or $K_2CO_3$;

the transition metal catalyst employed in Step A, part (ii) is $Pd_2dba_3$;

the optional phosphine ligand employed in Step A, part (ii) is Am-phos;

Step B, part (i) is conducted at a temperature in a range of from about 15° C. to about 30° C.;

the organic solvent employed in step B is an organic alcohol;

the inorganic base employed in step B is an alkali metal carbonate base;

Step D, part (ii) is conducted at a temperature in a range of from about 35° C. to about 50° C.;

Step C is conducted at a temperature in a range of from about 15° C. to about 35° C.;

the organic solvent employed in step C is acetonitrile;

the additive employed in step C is HOBt;

the non-nucleophilic base employed in step C is N-methylmorpholine;

the amide coupling reagent employed in step C is N-(3-dimethylaminopropyl)-N'-ethylcarbodiimide hydrochloride.

5. The process according to claim 4, wherein:

Step A, part (i) is conducted at a temperature in a range of from about 70° C. to about 90° C.;

the organic solvent employed in step A, part (i) is a mixture of DME and water;

the acetate or pivalate base employed in Step A, part (i) is selected from NaOAc, CsOAc and potassium acetate;

the transition metal catalyst employed in Step A, part (i) is $Pd_2dba_3$;

the optional phosphine ligand employed in Step A, part (i) is N-Bu(Ad)$_2$P;

Step A, part (ii) is conducted at a temperature in a range of from about 70° C. to about 90° C.;

the organic solvent employed in step A, part (ii) is a mixture of DME and water;

the carbonate, acetate or pivalate base employed in Step A, part (ii) is $Na_2CO_3$ or $K_2CO_3$;

the transition metal catalyst employed in Step A, part (ii) is $Pd_2dba_3$;

the optional phosphine ligand employed in Step A, part (ii) is Am-phos;

Step B, part (i) is conducted at a temperature in a range of from about 15° C. to about 30° C.;

the organic solvent employed in step B is an organic alcohol;

the inorganic base employed in step B is an alkali metal carbonate base;

Step B, part (ii) is conducted at a temperature in a range of from about 35° C. to about 50° C.;

Step C is conducted at a temperature in a range of from about 15° C. to about 35° C.;

the organic solvent employed in step C is acetonitrile;

the additive employed in step C is HOBt;

the non-nucleophilic base employed in step C is N-methylmorpholine;

the amide coupling reagent employed in step C is N-(3-dimethylaminopropyl)-N'-ethylcarbodiimide hydrochloride.

6. A process for preparing Compound A:

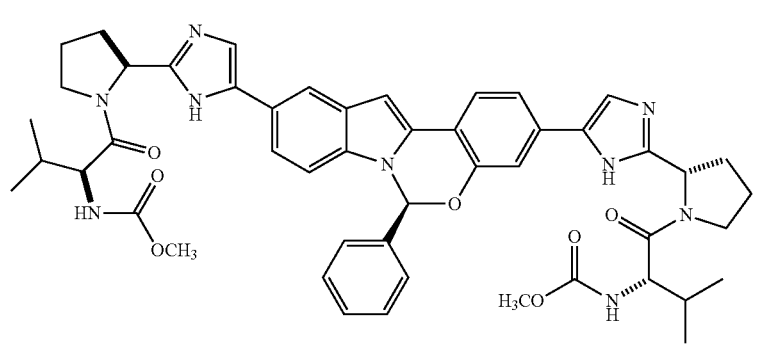

Compound A wherein said process comprises the steps:
(A) contacting an intermediate compound of formula VII:

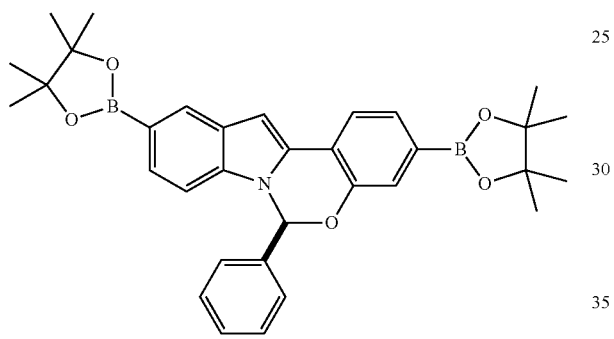

(VII)

with a compound of formula VIIb

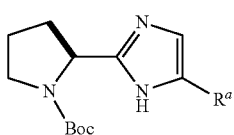

(VIIb)

wherein $R^a$ is Br, Cl or I,
in the presence of a carbonate, acetate or pivalate base and a transition metal catalyst, and optionally in the presence of a phosphorus ligand source, in said mixture of water and organic solvent E, to provide a compound of formula VIII:

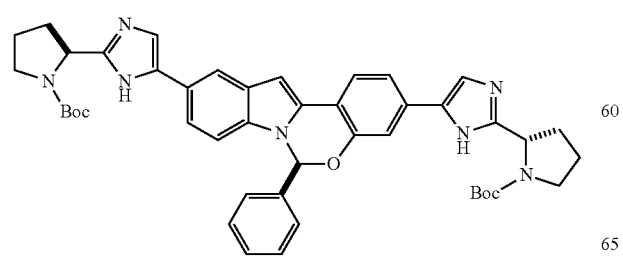

(VIII)

wherein organic solvent E is selected from dimethylacetamide, toluene, acetonitrile, N,N-dimethylformamide, tetrahydrofuran, 2-methyl tetrahydrofuran, cyclopentyl methyl ether, isopropanol, ethanol, ethyl acetate, isopropyl acetate and dimethoxyethane; and (D) (i) contacting the di-p-nitrobenzoate salt of the compound of Formula VIII with an inorganic base, in an organic solvent F, for a time sufficient to remove the Boc protecting groups from the compound of Formula VIII, then (ii) contacting the deprotected compound in situ with HCl to provide a compound of Formula IX:

(IX)

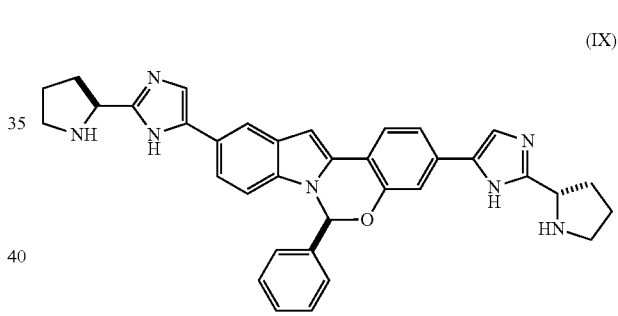

wherein organic solvent F is selected from methanol, acetonitrile, tetrahydrofuran, 2-methyl tetrahydrofuran, ethanol, isopropanol and toluene; and (E) contacting the compound of Formula IX with: (i) an additive selected from 2-hydroxypyridine-N-oxide, N-hydroxysuccinimide, HOBt and pyridine, and (ii) a non-nucleophilic base) in the presence of (i) a compound of formula Xa:

(Xa)

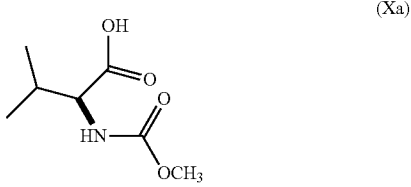

and (ii) an amide coupling reagent in an organic solvent G to provide Compound A, wherein organic solvent G is selected from tetrahydrofuran, N,N-dimethylformamide, dimethylacetamide, N-methylpyrrolidinone and dimethylsulfoxide.

7. The process of claim 1, wherein each occurrence of $R^1$ is methyl and each occurrence of $R^2$ is isopropyl.

8. The process of claim 1, wherein for compound (VIIb), $R^a$ is Br.

9. The process of claim 1, wherein for compound (VIIb), $R^a$ is Cl.

10. The process of claim 1, wherein for compound (VIIb), $R^a$ is I.

\* \* \* \* \*